US007132273B1

(12) United States Patent
Choi et al.

(10) Patent No.: US 7,132,273 B1
(45) Date of Patent: Nov. 7, 2006

(54) CELL WALL ANCHOR PROTEINS DERIVED FROM YEAST, GENES THEREOF AND CELL SURFACE EXPRESSION SYSTEMS USING THE SAME

(75) Inventors: Eui-Sung Choi, Daejon-si (KR); Jung-Hoon Sohn, Daejon-si (KR); So-Young Kim, Kimpo-si (KR)

(73) Assignee: Korea Research Institute of Bioscience and Biotechnology (KR)

( * ) Notice: Subject to any disclaimer, the term of this patent is extended or adjusted under 35 U.S.C. 154(b) by 216 days.

(21) Appl. No.: 10/333,951

(22) PCT Filed: Jul. 27, 2000

(86) PCT No.: PCT/KR00/00819

§ 371 (c)(1),
(2), (4) Date: Jan. 24, 2003

(87) PCT Pub. No.: WO02/12509

PCT Pub. Date: Feb. 14, 2002

(30) Foreign Application Priority Data

Jul. 26, 2000 (KR) .............................. 2000-42939

(51) Int. Cl.
*C12N 1/20* (2006.01)
*C12N 15/00* (2006.01)
*C12N 1/14* (2006.01)
*C12P 21/04* (2006.01)
*C12Q 1/00* (2006.01)
*C07K 1/00* (2006.01)
*C07H 21/04* (2006.01)
*C12Q 1/68* (2006.01)

(52) U.S. Cl. ..................... 435/252.3; 435/4; 435/6; 435/320.1; 435/69.1; 435/71.1; 435/254.1; 435/440; 530/350; 536/23.7; 536/23.2

(58) Field of Classification Search ................ 530/350; 435/252.2, 320.1, 252.33, 69.1, 71.1, 252.3, 435/254.1, 4, 6, 440, 350; 536/23.2, 23.7
See application file for complete search history.

(56) References Cited

U.S. PATENT DOCUMENTS 5,223,408 A 6/1993 Goeddel et al.

(Continued)

OTHER PUBLICATIONS

Toh-e et al Three yeast genes, PIR1, PIR2 and PIR3, containing internal tandem repeats, are related to each other, and PIR1 and PIR2 are required for tolerance to heat shock. Yeast. May 1993;9(5):481-94.*

(Continued)

*Primary Examiner*—Tekchand Saidha
*Assistant Examiner*—Yong D. Pak
(74) *Attorney, Agent, or Firm*—Lucas & Mercanti, LLP

(57) ABSTRACT

The present invention provides novel cell wall anchor proteins derived from yeast, genes thereof and the genetic method for tethering polypeptide to the yeast cell wall using the same. Particularly, the present invention provides the novel GPI (glycosyl phosphatidyl inositol)-anchor protein genes, SFD1, GAS1, TIP1 and CWP1, and their proteins, PIR2 cell wall protein gene and its protein derived from *Hansenula polymorpha*, and the cell surface expression system using them which immobilize foreign enzymes or polypeptides on the cell wall of a microbial cell. In addition, the present invention provides the cell surface expression system using WSC1 gene and its protein derived from yeasts, including *Hansenula polymorpha* and *Saccharomyces cerevisiae*, and STA1 gene and its protein derived from *Saccharomyces diastaticus*. The cell surface expression system of the present invention expects an immobilization effect as biocatalysts by adhereing a desired protein to the cell surface, and provides a means of altering target protein characteristics such as binding affinity and stability by library screening.

8 Claims, 15 Drawing Sheets

U.S. PATENT DOCUMENTS 5,223,409 A    6/1993    Ladner et al.
5,602,034 A    2/1997    Tekamp-Olson
6,114,147 A    9/2000    Frenken et al.

OTHER PUBLICATIONS

Vaart et al. Identification of three mannoproteins in the cell wall of *Saccharomyces cerevisiae*. J Bacteriol. Jun. 1995;177(11):3104-10.*

Shimoi, Hitoshi, et al., "Sedlp Is a Major Cell Wall Protein of *Saccharomyces cerevisiae* in the Stationary Phase and Is Involved in Lytic Enzyme Resistance" Journal of Bacteriology, Jul. 1998, p. 3381.

Rodriguez-Pena, et al., A novel family of cell wall-related proteins regulated differently during the yeast life cycle, Molecular and Cellular Biology, May 2000, p. 3245-3255.

Murai, T., et al., Assimilation of Cellooligosaccharides by a cell surface-engineered yeast expressing beta-glucosidase and carboxymethylcellulase from *Aspergillus aculeatus*, Applied and Environmental Microbiology, Dec. 1998, p. 4457-4861.

* cited by examiner

L3262 SS-CMC

L3262 SS-8-CMC

L3262 SS-8-TS-CMC

L3262 SS-TS-CMC

SEQUENCE LISTING

```
<160> NUMBER OF SEQ ID NOS: 15

<210> SEQ ID NO 1
<211> LENGTH: 396
<212> TYPE: DNA
<213> ORGANISM: Hansenula polymorpha

<400> SEQUENCE: 1
atgcaattca gaactttggc tccacttgct ttggcttccg ctgctttcgc tgcttactct      60
aacggcaccg tctccaccat tacttacgag accaccgttt ctgaggtcgt tactgctttg     120
actacctact gcccagaagc cacctctatc gtcaccaacg gaaagaccta cactgtcact     180
ggtgccacca ccttgaccat caccgactgc ccatgcacta agaagaaggt catcaccacc     240
accactgtca ccaccatccc agctaaatct tccactgctg cttcctctgt tgctgcttcc     300
tctgctccag tcatctccac tgccgagaac gctggtgcta aggttggtgc tgctggtttg     360
gctgcccttg ccggtgctgc tgctttcttg ctctaa                              396

<210> SEQ ID NO 2
<211> LENGTH: 9
<212> TYPE: PRT
<213> ORGANISM: Hansenula polymorpha

<400> SEQUENCE: 2

Ser Gln Ile Gly Asp Gly Gln Ile Gln
 1               5

<210> SEQ ID NO 3
<211> LENGTH: 13
<212> TYPE: PRT
<213> ORGANISM: Hansenula polymorpha
<220> FEATURE:
<221> NAME/KEY: MOD_RES
<222> LOCATION: (4)
```

<223> OTHER INFORMATION: Any amino acid

<400> SEQUENCE: 3

Gly Val Val Xaa Gln Ile Gly Asp Gly Gln Ile Gln Ala
1               5                   10

<210> SEQ ID NO 4
<211> LENGTH: 1014
<212> TYPE: DNA
<213> ORGANISM: Hansenula polymorpha

<400> SEQUENCE: 4

| | | |
|---|---|---|
| atgaagttca catcctcgct cgctgccatc agtttggcct ccaacgcatt cgctgcctat | 60 |
| gttggctcta cctactggac taccatgacc ccatcctaca ccctggatgg tgctctgact | 120 |
| agctactcgg ctactttcgg tattgctgtt gaaccactag agaccagttc ctcggtttcc | 180 |
| gcctctctca acgttgagaa agacaggtt gtttctcaaa ttggtgatgg tcaaattcag | 240 |
| gctaccacga acaccgagaa agaaacctcc aaatcctcta cttctactgc cgcagctgtt | 300 |
| gtgtcgcaaa tcacggacgg tcaaatccaa gccaccactg ccaccaccac ctcttcttca | 360 |
| tcgagctcca agaagactgc cgcagctgtt gtcactcaaa ttggsgacgg tcaaatccaa | 420 |
| gctaccacct ccacttcttc caagagcact gctgctgacg ttgttaccca aatcggcgat | 480 |
| ggtcagatcc aagccaccag caagtcgtca tccacttcca ctgctgctga cgttgtgtct | 540 |
| cagatcactg acggccagat ccaagctacc accagcacca aggcctcttc tgccaccacc | 600 |
| agcggtgtga tctcccagat ctccgacggt caaatccagg catcttccac cgcttcttcg | 660 |
| aagacctcca ccgcttcctc atccactgca actggagact acgtcacctc tgtgtcctgt | 720 |
| aagaaggagg gtgctctggc catgactttg aaggacggta tcctgtatga ctcggaggga | 780 |
| agaattggct ctatcgttgc taacagacaa ttccaattcg acggtcctcc accacaagct | 840 |
| ggtgccatct atgctgacgg atggtccatt tccccagacg gatacctggc cattggtaac | 900 |
| gacaccatat tctaccagtg tctgtcgggc accttctaca acttgtacga ccagtcgatt | 960 |
| ggaggccaat gtaataaggt ccacttgaag gctgtcgagt tggtcgactg ttag | 1014 |

<210> SEQ ID NO 5
<211> LENGTH: 1614
<212> TYPE: DNA
<213> ORGANISM: Hansenula polymorpha

<400> SEQUENCE: 5

| | | |
|---|---|---|
| atgcagctaa atctatcct ctcgctcacg ggcctgctct ccaccacgct ggctctgcct | 60 |
| accattgacg tggtgtccaa caagttcttc tattcgaaca cgggtcccca attctacgtc | 120 |
| aaaggtgtcg cgtaccagaa gaacacagaa atgctaccg acgacgcaac ttatgtcgat | 180 |
| ccgctcgctg acgaagattc gtgcaagaga gacatcccgt acttacagaa ccttggcatc | 240 |
| aatgttatcc gggtgtatgc agtcgatgcc tccaaggacc acgacggatg catgtctctg | 300 |
| ctcgaggatg ctggaatcta tgtgatctcc gatctttcga ccccaaacga gtcgatcgag | 360 |
| accaccagtc cgtcctggac tgtcgatctg tacaacagat atgccacggt gatcgatatg | 420 |
| ttccaaagct acgacaacgt gctcggcttt tttgcaggta atgaggttat caccaacaag | 480 |
| accaacagtg acgctgctcc gttcgtcaag gccgctatca gagacatgaa gcagtacatg | 540 |
| aaggacaaca actacagaga cattccgatc ggctactcgg ccaacgacga tgccaacacc | 600 |
| agagttccgt ctgcggacta cttctcctgt ggaaacgacg acgtcaaggc agacttttac | 660 |

-continued

```
ggtatcaaca tgtacgagtg gtgtggaaat gccacgttct caagctccgg ctacgaggcg      720
agaacgaagg aattttccaa tttgacgatc ccgatctttt tctcagagta cggttgcaac      780
agcgtcaagc cacgtgagtt cacagaggtg caagctatct actccgatga aatgacagac      840
gtttggtccg gcggtatcgt gtacatgtac ttccaggaag agaacgacta cggcctcgtt      900
tccatcaaag acaatgctgt ctcgactttg ggcgactaca ctaacctcaa gagtgagctc      960
gcgaaaatta gccctaccac ggcgtctgcc tctgctgcat cgcagtctgc cacagaattg     1020
agttgtccaa ccagccagag caactggaag catccacag accttcctcc aactccaaat     1080
gaggccgtgt gcgactgtct tgagtcgtcg ctcaaatgtg tcgtctccga cagcgtcgac     1140
tccgacgact acggcgactt cttcggtatc gtctgcgatc tcaccgactg ttctcaaatt     1200
tccaccagcg gcagtaacgg ctcctacggc gcatactcgt actgctcagc caaggacaag     1260
ctttcgttcc tgctcaacaa atactacgag gaacaggact ccaactcgtc ggcttgcgac     1320
ttcagcggct ctgcctcgct caataccaac ggctcgacac atccagctg ctcttcctta     1380 ttgagctctg cctcggcctc tccatcggcc actggctcct caaactcctc ccctgcatct     1440
ggctccggct ctagttccgg ctccagctcc ggctctggct ccagcagctc cagctcctcg     1500
tcgtcgtctg ccggcgcggg tgtcaacgct gtcccattgt cggccccaca attgggcctg     1560
ctctccttgt tctccacctt cttcttgggc ggactctcct acatctttat ctag           1614
```

<210> SEQ ID NO 6
<211> LENGTH: 852
<212> TYPE: DNA
<213> ORGANISM: Hansenula polymorpha

<400> SEQUENCE: 6

```
atgctctcgt ttaaaactct tgcgctacta gctttcgctc ttactgccgt ttctgctgcc       60
cctcaggctg acccatttgc ttttgctaat gcaatcggac ttccagttgc agcagaggca      120
acttacgctt gtcatgcctc ttgtggttac gctatttag ctgctcgtca atgttcccca      180
actggctccg aggacgctaa ctacaactcc acctgtctgt gtgcttccga cagtcaattc      240
ttgtcctacg tcccagcctg ccttgactgt ggatggtgtc tgtggagtga ctacggatcc      300
ttcttgacct ctgcttttggc tgaatgtcac accaacaccc agccaactgg tactacttgt      360
gccccaagca ctgctcaagc cgctgctacc tcttctgttg ctgctgcagc cagtgaagtc      420
tcttcttcgt cggctgctgc ttcttcaact caggctgccg ctgctgcttc cacttctgct      480
gctgcctcga ctgaggccac tacttccgct gctgctgctg ctacttcttc ctctgaggct      540
gctagctcat ctgcccatgt tcatagccat gctgctgagt ccacctccgc tgttgagtcc      600
acttccgctc tcactcccca tgctgctgag tcgactccgc tgctcattc ccatgctgtc      660 gaatccagct ccgctgctca tgttcattcc catgccgccg aatccagctc cgctgctcac      720
agccacgctc tggatctag ctccgctgca tccaactcta gtggacatat ctccactttc      780
tcgggagctg gtgctaaact cgccgttgga gccggagccg gtattgtcgg tcttgcagct      840
ctgcttatgt aa                                                          852
```

<210> SEQ ID NO 7
<211> LENGTH: 246
<212> TYPE: DNA
<213> ORGANISM: Hansenula polymorpha

<400> SEQUENCE: 7

```
atgtcctggc ttacactatt ggtgacgcca gcggttctgc tgcctttcta ctctgctctg       60
```

```
tacgagaaaa ctgctgcagc tcagtcttct cagtactcta gcagccctgc agctgtctct    120
tcaagaagct ctgcagctgc ctcttctagt gccaaaattg ctacttacga gggtgctgct    180
gccgagaatg ttgctaaggt cggcatgggt gctttgctgt cgggaatggc cgttcttctt    240
atgtaa                                                                246

<210> SEQ ID NO 8
<211> LENGTH: 1119
<212> TYPE: DNA
<213> ORGANISM: Hansenula polymorpha
<220> FEATURE:
<221> NAME/KEY: misc_feature
<222> LOCATION: (43)..(294)
<223> OTHER INFORMATION: coding for cystine motif
<220> FEATURE:
<221> NAME/KEY: misc_feature
<222> LOCATION: (760)..(873)
<223> OTHER INFORMATION: coding for transmembrane domain

<400> SEQUENCE: 8
atgagattcg gtgtcgtatt cgtgatcacc caagtcctag cagactttac gtatttaggt     60
tgctacagct cggatgccat ttccggcttg accaagaagg actcgtacac atggcagagc    120
tccagccatt gcacggagca gtgttcggga cacgcagttg ctgcattgat caacggccag    180
gactgttatt gcggagacga cgtaccttcg acaaccccg acggctcgtg cacaacgtcc    240
tgcactggtt atcccatgga gaagtgtggt ggtagcgact cttattccgt ctatgttgac    300
gagtctgagg aaaacgacga cgacagttcg tcggcgcagt cgtcgcactc gtccacagac    360
gatgccactt ccacctcctc cacctccacc acctcctcct ccagttccag tctgtccagc    420
tcctcaacat cgtcttcctc caagcaaagt tcctccccac agagctccac catgtcttcc    480
acagactcgt ctccaacgtc ctcaagtctg tccgctagct cgactacaac aagctcgatt    540
tcgtcctttt ctttctccca gagctcgtcg tcgtcttcaa ccacctcttc gtccacaccc    600
tcatccgaat cagtgcggat aactacgtcc gtttcacctg gaaacatgca gacctcgatc    660
atctacatca cgcagtccgt cgctacagcc acctcggcgt cggctgccgc gtcgtcctca    720
agtgcctcga gcgccaacaa caggtccacg gggctcagca agggcgcgaa ggccggaatc    780
gctgtcgggt cgatcctcgg agctttgctg ctcttgggac tcctgctcct gttcctgttt    840
tggcgcagac gccagcgcga cgacagagac aaccttagcg aaaagcgcgc atccagcatt    900
ttggcgtcgt cttcccgtca gcctccagct ggctcgcgag gtgcggcagc aggaatcgga    960
gccaaccgca ttcggattca tgtccgagga cgacagactg acatgccgg gcacgtcgag   1020 acggttcagc gacggttcgt tgccgggacg ctgccgctgg agccgcggtg ccgccgaata   1080
gtgcccgaca ggaggtttgc gggtggtaaa cccagatct                          1119

<210> SEQ ID NO 9
<211> LENGTH: 2337
<212> TYPE: DNA
<213> ORGANISM: Hansenula polymorpha
<220> FEATURE:
<221> NAME/KEY: misc_feature
<222> LOCATION: (1)..(96)
<223> OTHER INFORMATION: coding for secretion signal sequence
<220> FEATURE:
<221> NAME/KEY: misc_feature
<222> LOCATION: (97)..(120)
<223> OTHER INFORMATION: coding for octapeptide
<220> FEATURE:
<221> NAME/KEY: misc_feature
<222> LOCATION: (121)..(882)
```

<223> OTHER INFORMATION: coding for serine/threonine rich domain

<400> SEQUENCE: 9

```
atggtaggcc tcaaaaatcc atatacgcac actatgcaaa gaccatttct actcgcttat      60
ttggtccttt cgcttctatt taactcagct ttgggttttc caactgcact agttcctaga     120
ggatcctcct ctagcaacat cacttcctcc ggtccatctt caactccatt cagctctgct     180
actgaaagct tttctactgg cactactgtc actccatcat catccaaata ccctggcagt     240
aaaacagaaa cttctgtttc ttctacaacc gaaactacca ttgttccaac tacaactacg     300
acttctgtca taacaccatc aacaaccact attaccacta cggtttgctc tacaggaaca     360
aactctgccg gtgaaactac ttctggatgc tctccaaaga ccattacaac tactgttcca     420
tgttcaacca gtccaagcga accgcatcg gaatcaacaa ccacttcacc taccacacct      480
gtaactacag ttgtctcaac caccgtcgtt actactgagt attctactag tacaaaacaa     540
ggtggtgaaa ttacaactac atttgtcacc aaaaacattc caaccactta cctaactaca     600
attgctccaa cttcatcagt cactacggtt accaatttca ccccaaccac tattactact     660
acggtttgct ctacaggaac aaactctgcc ggtgaaacta cctctggatg ctctccaaag     720
actgtcacaa caactgttcc ttgttcaact ggtactggcg aatacactac tgaagctacc     780
gcccctgtta acagctgt cacaaccacc gttgttacca ctgaatcctc tacgggtact      840
aactccgctg gtaagacgac aactagttac acaacaaagt ctgtaccaac cacctatgta     900
tttgactttg gcaagggcat tctcgatcaa agctgcggcg tgtattttc aaacaacggc      960
tcttcgcaag tgcagctgcg ggatgtagtc ttgatgaatg ggacagtggt atacgattca    1020
aacgcgcctt gggacagtag tgcgctggag gagtggctcc agcgacagaa aaagtttcc    1080
atcgaaagaa tatttgaaaa tattgggccc agcgccgtgt atccgtctat tttgcctggg    1140
gtcgtgattg cgtcaccatc gcaaacgcat ccagactact tctaccaatg gataagggac    1200
agcgcgttga cgataaacag tattgtctct cattctgcgg acccggcaat agagacgtta    1260
ttgcagtacc tgaacgtttc attccacttg caaagaacca acaacacatt gggcgctggc    1320
attggttaca ctaacgatac agtggctttg ggagaccta agtggaacgt cgacaacacg    1380
gctttcacgg aaccttgggg tcgtcctcaa aacgatggcc ctgctcttcg aagcattgcc    1440
atcttaaaaa tcatcgacta catcaagcaa tctggcactg atctgggggc caagtaccca    1500
ttccagtcca ccgcagatat ctttgatgat attgtacgtt gggacctgag gttcattatt    1560
gaccactgga attcttccgg atttgatcta tgggaggaag tcaatggcat gcatttcttt    1620
actttactgg tacaactgtc tgcagtggac aggtcgctgt cgtattttaa cgcctcagaa    1680
cggtcgtctc cctttgttga agaattgcgt cagacacgcc gggacatctc caagttttta    1740
gtggaccctg cgaatgggtt tatcaacggc aagtacaatt atattgttga cacccatg     1800
attgccgaca cattgagatc cggactggac atatccactt tattagctgc gaacaccgtc    1860
cacgatgcgc catctgcttc ccatcttccg ttcgatatca atgaccctgc cgtcctgaac    1920
acgttgcacc atttgatgtt gcacatgcgt tcgatatacc ccatcaacga tagctccaaa    1980
aatgcaacgg gtattgccct gggccggtat cctgaggacg tatatgatgg atatggcgtt    2040
ggcgagggaa atccctgggt cctggccacg tgtgccgctt caacaacgct ttatcagctc    2100
atttacagac acatctctga gcagcatgac ttggttgtcc aatgaacaa cgattgttcg     2160
aacgcatttt ggagcgagct ggtattctcc aacctcacga ctttgggaaa tgacgaaggc    2220
tatttgattt tggagttcaa tacacctgcc ttcaatcaaa ccatacaaaa aatcttccaa    2280
```
ctagctgatt cattcttggt caagctgaaa gccacgtggg aacagacggg gaactaa    2337

<210> SEQ ID NO 10
<211> LENGTH: 8
<212> TYPE: PRT
<213> ORGANISM: Saccharomyces diastaticus

<400> SEQUENCE: 10

Phe Pro Thr Ala Leu Val Pro Arg
 1               5

<210> SEQ ID NO 11
<211> LENGTH: 131
<212> TYPE: PRT
<213> ORGANISM: Hasenula polymorpha

<400> SEQUENCE: 11

Met Gln Phe Arg Thr Leu Ala Pro Leu Ala Leu Ala Ser Ala Ala Phe
 1               5                  10                  15

Ala Ala Tyr Ser Asn Gly Thr Val Ser Thr Ile Thr Tyr Glu Thr Thr
             20                  25                  30

Val Ser Glu Val Val Thr Ala Leu Thr Thr Tyr Cys Pro Glu Ala Thr
         35                  40                  45

Ser Ile Val Thr Asn Gly Lys Thr Tyr Thr Val Thr Gly Ala Thr Thr
     50                  55                  60

Leu Thr Ile Thr Asp Cys Pro Cys Thr Lys Lys Val Ile Thr Thr
 65                  70                  75                  80

Thr Thr Val Thr Thr Ile Pro Ala Lys Ser Ser Thr Ala Ala Ser Ser
                 85                  90                  95

Val Ala Ala Ser Ser Ala Pro Val Ile Ser Thr Ala Glu Asn Ala Gly
             100                 105                 110

Ala Lys Val Gly Ala Ala Gly Leu Ala Ala Leu Ala Gly Ala Ala Ala
         115                 120                 125

Phe Leu Leu
     130

<210> SEQ ID NO 12
<211> LENGTH: 337
<212> TYPE: PRT
<213> ORGANISM: Hansenula polymorpha

<400> SEQUENCE: 12

Met Lys Phe Thr Ser Ser Leu Ala Ala Ile Ser Leu Ala Ser Asn Ala
 1               5                  10                  15

Phe Ala Ala Tyr Val Gly Ser Thr Tyr Trp Thr Thr Met Thr Pro Ser
             20                  25                  30

Tyr Thr Leu Asp Gly Ala Leu Thr Ser Tyr Ser Ala Thr Phe Gly Ile
         35                  40                  45

Ala Val Glu Pro Leu Glu Thr Ser Ser Val Ser Ala Ser Leu Asn
     50                  55                  60

Val Glu Lys Arg Gln Val Val Ser Gln Ile Gly Asp Gly Gln Ile Gln
 65                  70                  75                  80

Ala Thr Thr Asn Thr Glu Lys Glu Thr Ser Lys Ser Ser Thr Ser Thr
                 85                  90                  95

Ala Ala Ala Val Val Ser Gln Ile Thr Asp Gly Gln Ile Gln Ala Thr
             100                 105                 110

Thr Ala Thr Thr Thr Ser Ser Ser Ser Ser Lys Lys Thr Ala Ala
         115                 120                 125

```
Ala Val Val Thr Gln Ile Gly Asp Gly Gln Ile Gln Ala Thr Thr Ser
130                 135                 140

Thr Ser Ser Lys Ser Thr Ala Ala Asp Val Val Thr Gln Ile Gly Asp
145                 150                 155                 160

Gly Gln Ile Gln Ala Thr Ser Lys Ser Ser Thr Ser Thr Ala Ala
                165                 170                 175

Asp Val Val Ser Gln Ile Thr Asp Gly Gln Ile Gln Ala Thr Thr Ser
                180                 185                 190

Thr Lys Ala Ser Ser Ala Thr Ser Gly Val Ile Ser Gln Ile Ser
            195                 200                 205

Asp Gly Gln Ile Gln Ala Ser Ser Thr Ala Ser Ser Lys Thr Ser Thr
210                 215                 220

Ala Ser Ser Thr Ala Thr Gly Asp Tyr Val Thr Ser Val Ser Cys
225                 230                 235                 240

Lys Lys Glu Gly Ala Leu Ala Met Thr Leu Lys Asp Gly Ile Leu Tyr
                245                 250                 255

Asp Ser Glu Gly Arg Ile Gly Ser Ile Val Ala Asn Arg Gln Phe Gln
                260                 265                 270

Phe Asp Gly Pro Pro Gln Ala Gly Ala Ile Tyr Ala Asp Gly Trp
            275                 280                 285

Ser Ile Ser Pro Asp Gly Tyr Leu Ala Ile Gly Asn Asp Thr Ile Phe
290                 295                 300

Tyr Gln Cys Leu Ser Gly Thr Phe Tyr Asn Leu Tyr Asp Gln Ser Ile
305                 310                 315                 320

Gly Gly Gln Cys Asn Lys Val His Leu Lys Ala Val Glu Leu Val Asp
                325                 330                 335

Cys

<210> SEQ ID NO 13
<211> LENGTH: 283
<212> TYPE: PRT
<213> ORGANISM: Hansenula polymorpha

<400> SEQUENCE: 13

Met Leu Ser Phe Lys Thr Leu Cys Ala Thr Ala Phe Ala Leu Thr Ala
1               5                   10                  15

Val Ser Ala Ala Pro Gln Ala Asp Pro Phe Ala Phe Ala Asn Ala Ile
                20                  25                  30

Gly Leu Pro Val Ala Ala Glu Ala Thr Tyr Ala Cys His Ala Ser Cys
            35                  40                  45

Gly Tyr Ala Ile Leu Ala Ala Arg Gln Cys Ser Pro Thr Gly Ser Glu
50                  55                  60

Asp Ala Asn Tyr Asn Ser Thr Cys Leu Cys Ala Ser Asp Ser Gln Phe
65                  70                  75                  80

Leu Ser Tyr Val Pro Ala Cys Leu Asp Cys Gly Trp Cys Leu Trp Ser
                85                  90                  95

Asp Tyr Gly Ser Phe Leu Thr Ser Ala Leu Ala Glu Cys His Thr Asn
            100                 105                 110

Thr Gln Pro Thr Gly Thr Thr Cys Ala Pro Ser Thr Ala Gln Ala Ala
        115                 120                 125

Ala Thr Ser Ser Val Ala Ala Ala Ser Glu Val Ser Ser Ser Ser
130                 135                 140

Ala Ala Ala Ser Ser Thr Gln Ala Ala Ala Ala Ser Thr Ser Ala
145                 150                 155                 160
```

```
Ala Ala Ser Thr Glu Ala Thr Ser Ala Ala Ala Ala Thr Ser
            165                 170                 175

Ser Ser Glu Ala Ala Ser Ser Ala His Val His Ser His Ala Ala
        180                 185                 190

Glu Ser Thr Ser Ala Val Glu Ser Thr Ser Ala Ala His Ser His Ala
        195                 200                 205

Ala Glu Ser Ser Ser Ala Ala His Ser His Ala Val Glu Ser Ser Ser
210                 215                 220

Ala Ala His Val His Ser His Ala Ala Glu Ser Ser Ser Ala Ala His
225                 230                 235                 240

Ser His Ala Ala Gly Ser Ser Ala Ala Ser Asn Ser Ser Gly His
            245                 250                 255

Ile Ser Thr Phe Ser Gly Ala Gly Ala Lys Leu Ala Val Gly Ala Gly
            260                 265                 270

Ala Gly Ile Val Gly Leu Ala Ala Leu Leu Met
            275                 280

<210> SEQ ID NO 14
<211> LENGTH: 537
<212> TYPE: PRT
<213> ORGANISM: Hansenula polymorpha

<400> SEQUENCE: 14

Met Gln Leu Lys Ser Ile Leu Ser Leu Thr Gly Leu Leu Ser Thr Thr
  1               5                  10                  15

Leu Ala Leu Pro Thr Ile Asp Val Val Ser Asn Lys Phe Phe Tyr Ser
            20                  25                  30

Asn Asn Gly Ser Gln Phe Tyr Val Lys Gly Val Ala Tyr Gln Lys Asn
        35                  40                  45

Thr Glu Asn Ala Thr Asp Asp Ala Thr Tyr Val Asp Pro Leu Ala Asp
     50                  55                  60

Glu Asp Ser Cys Lys Arg Asp Ile Pro Tyr Leu Gln Asn Leu Gly Ile
 65                  70                  75                  80

Asn Val Ile Arg Val Tyr Ala Val Asp Ala Ser Lys Asp His Asp Gly
                 85                  90                  95

Cys Met Ser Leu Leu Glu Asp Ala Gly Ile Tyr Val Ile Ser Asp Leu
            100                 105                 110

Ser Thr Pro Asn Glu Ser Ile Glu Thr Thr Ser Pro Ser Trp Thr Val
        115                 120                 125

Asp Leu Tyr Asn Arg Tyr Ala Thr Val Ile Asp Met Phe Gln Ser Tyr
    130                 135                 140

Asp Asn Val Leu Gly Phe Phe Ala Gly Asn Glu Val Ile Thr Asn Lys
145                 150                 155                 160

Thr Asn Ser Asp Ala Ala Pro Phe Val Lys Ala Ala Ile Arg Asp Met
                165                 170                 175

Lys Gln Tyr Met Lys Asp Asn Tyr Arg Asp Ile Pro Ile Gly Tyr
            180                 185                 190

Ser Ala Asn Asp Asp Ala Asn Thr Arg Val Pro Ser Ala Asp Tyr Phe
        195                 200                 205

Ser Cys Gly Asn Asp Asp Val Lys Ala Asp Phe Tyr Gly Ile Asn Met
    210                 215                 220

Tyr Glu Trp Cys Gly Asn Ala Thr Phe Ser Ser Gly Tyr Glu Ala
225                 230                 235                 240

Arg Thr Lys Glu Phe Ser Asn Leu Thr Ile Pro Ile Phe Phe Ser Glu
                245                 250                 255
```

```
Tyr Gly Cys Asn Ser Val Lys Pro Arg Glu Phe Thr Glu Val Gln Ala
            260                 265                 270

Ile Tyr Ser Asp Glu Met Thr Asp Val Trp Ser Gly Gly Ile Val Tyr
        275                 280                 285

Met Tyr Phe Gln Glu Glu Asn Asp Tyr Gly Leu Val Ser Ile Lys Asp
    290                 295                 300

Asn Ala Val Ser Thr Leu Gly Asp Tyr Thr Asn Leu Lys Ser Glu Leu
305                 310                 315                 320

Ala Lys Ile Ser Pro Thr Thr Ala Ser Ala Ser Ala Ala Ser Gln Ser
                325                 330                 335

Ala Thr Glu Leu Ser Cys Pro Thr Ser Gln Ser Asn Trp Lys Ala Ser
            340                 345                 350

Thr Asp Leu Pro Pro Thr Pro Asn Glu Ala Val Cys Asp Cys Leu Glu
        355                 360                 365

Ser Ser Leu Lys Cys Val Val Ser Asp Ser Val Asp Ser Asp Asp Tyr
    370                 375                 380

Gly Asp Phe Phe Gly Ile Val Cys Asp Leu Thr Asp Cys Ser Gln Ile
385                 390                 395                 400

Ser Thr Ser Gly Ser Asn Gly Ser Tyr Gly Ala Tyr Ser Tyr Cys Ser
                405                 410                 415

Ala Lys Asp Lys Leu Ser Phe Leu Leu Asn Lys Tyr Tyr Glu Glu Gln
            420                 425                 430

Asp Ser Asn Ser Ser Ala Cys Asp Phe Ser Gly Ser Ala Ser Leu Asn
        435                 440                 445

Thr Asn Gly Ser Thr Ala Ser Ser Cys Ser Ser Leu Leu Ser Ser Ala
    450                 455                 460

Ser Ala Ser Pro Ser Ala Thr Gly Ser Ser Asn Ser Ser Pro Ala Ser
465                 470                 475                 480

Gly Ser Gly Ser Ser Ser Gly Ser Ser Ser Gly Ser Gly Ser Ser Ser
                485                 490                 495

Ser Ser Ser Ser Ser Ser Ser Ala Gly Ala Gly Val Asn Ala Val Pro
            500                 505                 510

Leu Ser Ala Pro Gln Leu Gly Leu Leu Ser Leu Phe Ser Thr Phe Phe
        515                 520                 525

Leu Gly Gly Leu Ser Tyr Ile Phe Ile
    530                 535

<210> SEQ ID NO 15
<211> LENGTH: 81
<212> TYPE: PRT
<213> ORGANISM: Hansenula polymorpha

<400> SEQUENCE: 15

Met Ser Trp Leu Thr Leu Leu Val Thr Pro Ala Val Leu Leu Pro Phe
  1               5                  10                  15

Tyr Ser Ala Leu Tyr Glu Lys Thr Ala Ala Ala Gln Ser Ser Gln Tyr
             20                  25                  30

Ser Ser Ser Pro Ala Ala Val Ser Ser Arg Ser Ser Ala Ala Ala Ser
         35                  40                  45

Ser Ser Ala Lys Ile Ala Thr Tyr Glu Gly Ala Ala Ala Glu Asn Val
     50                  55                  60

Ala Lys Val Gly Met Gly Ala Leu Leu Ser Gly Met Ala Val Leu Leu
 65                  70                  75                  80

Met
```

CELL WALL ANCHOR PROTEINS DERIVED FROM YEAST, GENES THEREOF AND CELL SURFACE EXPRESSION SYSTEMS USING THE SAME

This patent application claims a benefit of priority from Korean Patent Application No. 2000/42939 filed Jul. 26, 2000 through PCT Application Serial No. PCT/KR00/00819 filed Jul. 27, 2000, the contents of each of which are incorporated herein by reference.

FIELD OF THE INVENTION

The present invention relates to novel cell wall proteins derived from yeast, genes thereof, and surface expression systems using the same. More particularly, the present invention relates to surface expression systems using four *Hansenula polymorpha*-derived, GPI (glycosylphosphatidylinositol)-anchor proteins, HpSed1p, HpGas1p, HpTip1p and HpCwp1p, and a *Hansenula polymorpha*-derived cell wall protein, HpPir2p for the expression of foreign proteins onto the cell surface of *Hansenula polymorpha* and other yeasts. Also, the present invention relates to surface expression systems using proteins coded by *Hansenula polymorpha*-derived HpWSC1 and *Saccharomyces diastaticus*-derived STA1 for the expression of foreign proteins on the cell surface of *Hansenula polymorpha* and other yeasts.

BACKGROUND ART OF THE INVENTION

In recent years, active research have been directed to expression of desired foreign proteins on the surface of single cell organisms, such as bacteriophages, bacteria, and yeasts, because proteins expressed on the cell surface have various useful applications, including production of novel vaccines, screening of various antigens and antibodies, immobilization of useful enzymes onto the cell surface, and the like.

At first, the expression of foreign proteins on the cell surface was applied to the screening of epitopes and antigenicity-determining peptide fragments, with the aim of stable vaccine production. Before then, the production of vaccine had been achieved by the selection of the mutants, which showed stable and continuous titers from the randomly mutated pathogen library. However, the vaccines produced in the conventional manner are likely to lose their antigenicity when being administered via oral routes to humans or animals. Much effort has been made to overcome these problems using the live oral vaccines displayed on the cell surface.

In one strategy to express antigenic proteins on the cell surface, endogenous cell surface proteins are used to guide these proteins onto the cell surface. For example, a gene encoding a cell surface protein is fused to a gene encoding an antigenic protein, and the resulting recombinant gene is introduced into Gram-negative bacteria to express the fusion protein on the cell surface. The antigenic protein passenger in the fusion protein vehicle can act as an effective antigen to elicit immune responses. Especially, Gram-negative bacteria are very efficient for this purpose, because the lipopolysaccharide (LPS) presenting on their cell envelope enhances the antigenicity of the fusion protein expressed on the cell surface.

As a rule, proteins to be secreted or expressed on cell surfaces have secretion signals, which allow the nascent proteins to pass through the cytoplasmic membrane, in their primary sequence. To be expressed on the cell surface of Gram-negative bacteria, a protein translocates across the cytoplasmic membrane and the periplasmic space and embedded in the outer membrane so as to protrude to the outer membrane. In bacteria, several enzymes and toxins have secretion signals and (or) targeting signals, which induce the proteins to target regions. Therefore, using such a secretion signal or targeting signal with the suitable promoter can successfully perform localization of a foreign protein on cell surfaces.

Thus far, extensive attempts have been made to utilize surface proteins of Gram-negative bacteria in expressing foreign proteins of interest onto the cell surface. The surface proteins used for the localization of foreign proteins can be largely classified into outer membrane proteins, lipoproteins, secretory proteins, and cell surface organelle proteins.

LamB, PhoE and OmpA, known as outer membrane proteins of Gram-negative bacteria, have been used for the production of foreign proteins on cell surfaces. When the outer membrane proteins are employed, foreign proteins are limited in size, because they must be inserted into the loops protruded out of the cell surface. Additionally, since the C- and N-termini of the foreign proteins to be inserted are required to be located near each other in the three dimensional structure, both termini must be brought close to each other by the use of a peptide linkage when the distance therebetween is large.

In fact, where LamB or PhoE is used, insertion of a foreign polypeptide as large as or larger than 50–60 amino acids failed to construct a stable membrane protein by the steric hindrance. (Charbit et al., *J. Immunol.*, 1997, 139, 1658–1664; Agterberg et al., *Vaccine*, 1990, 8, 85–91). To solve this problem, an OmpA fragment containing a minimum target signal necessary for proper location was tried. For example, β-lactamase linked to the C-terminus of a target signal of OmpA was successfully expressed on the cell surface. Protein translocation from the cytoplasm to the outer membrane was achieved by the fusion of the signal sequence for the lipoprotein Lpp of *E. coli* to the N-terminus of OmpA (Francisco et al., *Proc. Natl. Acad. Sci. USA*, 1992, 489, 2713–2717).

As described above, use of bacterial outer membrane proteins in cell surface display of foreign proteins requires linkage between the foreign proteins and appropriate outer membrane proteins at a gene level, so as to synthesize fusion proteins capable of passing through the cytoplasmic membrane and being stably embedded in the outer membrane. Suitable surface anchoring motif is an outer membrane protein which satisfies the following requirements: 1) to have a secretion signal which allows the fusion protein to pass through the cytoplasmic membrane; 2) to have a target signal which allows the fusion protein to anchor in the outer membrane; 3) to be expressed on the outer membrane in large quantities; and 4) to be expressed stably irrespective of protein size. Thus far, a surface-anchoring motif, which meets all of the requirements, has not yet been developed.

Meanwhile, lipoproteins have also been used as a surface-anchoring motif. Especially, lipoprotein from *E. coli* is very useful, because it translocates across the inner membrane by the N-terminal secretion signals and directly linked to outer or inner membrane lipids via the covalent bond of its terminal L-cystein. Lpp, a major lipoprotein from *E. coli*, which is associated with the outer membrane at its N-terminus and with the cell wall peptidoglycan (PG) at its C-terminus, can be used to secrete and transport foreign proteins onto the surface of *E. coli* by fusion with the outer membrane protein A (OmpA, Francisco et al., *Proc. Natl. Acad. Sci. USA*, 1992, 489, 2713–2717). Another lipoprotein used in the surface expression of foreign protein is TraT. It was reported that TraT has been used to express peptides such as poliovial C3 epitope on the cell surface of E. coli (Felici et al., J. Mol. Biol., 1991, 222, 301–310). Additionally, a peptidoglycan-associated lipoprotein (PAL), whose function has not been elucidated clearly yet, was used for the surface expression of a recombinant antibody (Fuchs et al., Bio/Technology, 1991, 9, 1369–1372). In this case, C-terminus of the PAL was associated with peptidoglycan and N-terminus of it was fused to the recombinant antibody exposed on the cell surface.

Secretory proteins, which pass through the outer membrane, may be used as the surface anchor, but these are not well developed in Gram-negative bacteria. Only a few proteins have the secretory mechanisms by aid of the helper proteins. For instance, the lipoprotein pullulanase secreted from Klebsiella oxytoca is anchored on the outer membrane via a linkage between the lipid and its N-terminus, and completely secreted into a culture medium during the growth-resting phase. Kornacker et al. have been tried to express P-lactamase on the cell surface using the N-terminal fragment of pullulanase, but the expressed pullulanase-β-lactamase fusion protein was released to the cell media after short period of anchoring. When using alkaline phosphatase, a periplasmic space protein, as a target protein, the surface expression was not achieved. Functional expression of alkaline phosphatase appears to be difficult because at least 14 proteins are necessary for the secretion of this protein (Kornacker et al., Mol. Microl., 1990, 4, 1101–1109).

The IgA protease derived from Neisseria, a pathogenic microorganism possessing an interesting secretion system, has a secretion signal at the C-terminal beta-domain and this signal guides the N-terminal protease domain onto the cell surface. This protease is secreted into the culture medium by its own catalytic hydrolysis after being anchored on the outer membrane. Using the IgA protease beta-subunit, the 12 kDa form of cholera toxin B-subunit was surface expressed (Klauser et al., EMBO J., 1990, 9, 1991–1999). However, the protein folding occurred in the periplasmic space during the transport prevents the secretion of the fusion protein.

Proteins from cell surface organelles of Gram-negative bacteria, such as flagella, pili, and fimbriae, may be also available as surface anchoring motifs. For example, a flagellin, the subunit protein of flagellar filament, was used for the stable surface expression of cholera toxin B subunit and a B-type hepatitis viral peptide, and which were found to strongly react with their corresponding antibodies (Newton et al., Science, 1989, 244, 70–72). When using fimbrilin, a fimbria subunit protein, as a surface anchoring motif, only small size peptides were successfully expressed (Hedegaard et al., Gene, 1980, 85, 115–124).

Similar attempts have recently been developed in Gram-positive bacteria using surface proteins of Gram-positive and negative bacteria as surface anchoring motifs (Samuelson et al., J. Bacterial., 1995, 177, 1470–1476). A malaria blood stage antigen consisting of 80 amino acid residues and a albumin-associated protein from Streptococcus protein G were effectively expressed on the cell surface of Gram-positive bacteria using a surface expression system containing the Staphylococcus aureus-derived Protein A as a surface anchoring motif and a secretion signal from Staphylococcus hyicus-derived lipase.

As a result of extensive research on surface expression in Gram-positive and Gram-negative bacteria, various surface expression systems are developed and patented in the U.S.A., Europe, and Japan. In the past three years, eight patents concerning surface expression systems have been issued, among which, the case using outer membrane proteins of Gram-negative bacteria is five (WO9504069, WO9324636, WO9310214, EP603672 and U.S. Pat. No. 5,356,797), using a pilus, a cell surface organelle, is one (WO9410330), and using a cell surface lipoprotein is one (WO9504079).

The most widely used bacterial host for foreign protein production is E. coli because it is easy to culture and its gene structure is well known. Foreign proteins, however, are not well secreted into culture media under ordinary conditions of E. coli. Additionally, when foreign proteins are excessively expressed, they are accumulated as inclusion bodies within the cell. Accordingly, the purification of them requires a refolding process for solubilizing the inclusion bodies, which results in a significant reduction in yield. Further, since E. coli produces endotoxins harmful to the human body, the recombinant proteins may be contaminated with the toxins when being purified.

In contrast, yeast has been studied as a host for producing useful foreign proteins by genetic engineering techniques because it can easily secrete proteins in active forms into the culture media under the control of its own intracellular secretion system, which is operated in a manner similar to that of higher eucaryotic organisms.

Since the production of interferon in 1981 (Hitzeman et al., 1981, nature, 293; 717–722), yeast has been extensively utilized for the production of foreign proteins. In addition, not only were recombinant proteins of yeast approved by the FDA of the U.S.A. for their safety to the human body, but also most of the regulatory mechanisms of gene expression in yeast are known (Strathern et al., The Molecular Biology of the Yeast Saccharomyces, Metabolism and Gene Expression, Cold Spring Harbor Laboratory, N.Y., 1982). Accordingly, yeast system provides several significant advantages for the production of foreign proteins. For example, the proteins expressed in yeast are safe to the human body, and extracellularly secreted in conformations retaining high specific activity, similar to those expressed in animal or human cells. Furthermore, the purification processes for the proteins produced from yeast is simple compared to E. coli, and requires no refolding processes to obtain active forms, thus showing high production yield. Particularly, the surface expression in S. cerevisiae has recently been under extensive study. A few years ago, studies on the surface expression of foreign proteins in yeast were mainly focused on α-agglutinin, a typical cell wall protein as a surface anchoring motif (Schreuder et al., Yeast, 1993, 9, 399). In recent years, the study about surface anchoring motif has been extended to various cell wall proteins. Above all, the screening of surface anchor proteins through the conserved sequence analysis is extensively achieved, as the genome project for S. cerevisiae has been completed (Hamada et al., Mol. Gen. Genet., 1998, 258, 53). Using such surface proteins as surface anchoring motifs, various enzymes, including α-galactosidase, glucoamylase, lipase, and cutinase have been stably expressed on the cell surface of S. cerevisiae. In addition, expression of various enzymes on cell surface could develop many useful industrial biocatalysts (Murai et al., Appl. Microbiol. Biotechnol., 1999, 51, 65). A surface expression system using α-agglutinin as an anchoring motif has been developed and commercialized by Invitrogen Corporation. Furthermore, yeast, which is a eucaryotic microorganism usually harmless to the human body, is highly useful as a host for producing proteins for use in food or medical materials. For instance, B-type hepatitis viral antigen (HbsAg) was expressed on the yeast cell surface with the aim of developing live vaccines (Schreuder et al., *Vaccine*, 1996, 14, 383).

As mentioned above, active research has been directed to cell wall proteins throughout the world, but limited to *S. cerevisiae*. At present, researches on the cell wall proteins of other yeasts, such as *Candida albicans*, are in the initial stage. Therefore, there remains an urgent need for studies on surface proteins and surface expression thereof in industrially useful yeasts. Because the mediating proteins that have been studied thus far make use of glycosylphosphatidylinositol-anchor for surface anchoring, the proteins of interest must be linked to the anchor proteins at their carboxyl termini. However, some of the proteins may not exhibit their full activity under such a condition, and this is recognized as a drawback in yeast surface expression system.

SUMMARY OF THE INVENTION

Leading to the present invention, the intensive and thorough research on extracellular transport of exogenous proteins, conducted by the present inventors, resulted in the finding that surface proteins derived from *Hansenula polymorpha*, an industrially useful methanol-assimilating yeast, are highly effective in construction of surface expression systems and development of biocatalyst application systems. The surface expression system established in the present invention can stably express proteins of interest onto the cell surface, thus finding numerous applications in various fields, including immobilization of biocatalysts and large-scale production of proteins, such as enzymes, antigens, antibodies, etc.

Therefore, it is an object of the present invention to resolve the foregoing or other problems encountered in prior arts and to provide systems for the exportation of exogenous polypeptides to discrete regions of a host cell in which they are expressed, and uses thereof.

It is another object of the present invention to provide a novel surface anchor protein and its gene, derived from *Hansenula polymorpha*.

It is a further object of the present invention to provide a surface expression system using all or part of the surface proteins as mediators for surface expression of exogenous polypeptides or proteins.

It is still a further object of the present invention to provide an expression mediator protein, isolated form *Hansenula polymorpha*, which can be fused to the amino termini of proteins to be expressed on the cell surface, and a gene encoding the mediator protein.

It is still another object of the present invention to provide a surface expression system in which all or part of the expression mediator protein which can be fused to the amino termini of proteins to be expressed, is employed.

It is still another object of the present invention to provide a surface expression system in which all or part of the known surface protein derived from *Saccharomyces diastaticus* and *Hansenula polymorpha*, is employed.

In accordance with an aspect of the present invention, there are provided the isolated DNA sequences, containing the base sequence HpSED1 represented by the SEQ. ID. NO: 1, the base sequence HpRIR2 represented by the SEQ. ID. NO: 4, the base sequence HpGAS1 represented by the SEQ. ID. NO: 5, the base sequence HpTIP1 represented by the SEQ. ID. NO: 6, and the base sequence HpCWP1 represented by the SEQ. ID. NO: 7, all encoding novel cell wall proteins of *Hansenula polymorpha*, and their DNA homologues.

In accordance with another aspect of the present invention, there are provided novel *E. coli* strains harboring recombinant vector containing a 4 kb EcoRI fragment of the base sequence HpSED1, a 5.5 kb SalI fragment of the base sequence HpPIR2, a 3 kb PstI fragment of the base sequence HpGAS1, a 3.5 kb XbaI fragment of the base sequence HpTIP1, and a 6 kb SalI fragment of the base sequence HpCWP1.

In accordance with a further aspect of the present invention, there are provided surface expression systems in which base sequences of HpSED1, HpPIR2, HpGAS1, HpTIP1, HpCWP1, STA1 from *Saccharomyces diastaticus*, HpWSC1 from *Hansenula polymorpha* and WSC1 from *Saccharomyces cerevisiae* or their partial fragments are used to express mediator proteins which locate exogenous proteins onto the surface of a cell. Herein, useful in the present invention is a eukaryotic cell selected from the group consisting of yeast spp., including *Candida* spp., *Debaryomyces* spp., *Hansenula* spp., *Kluyveromyces* spp., *Pichia* spp., *Schizosaccharomyces* spp., *Yarrowia* spp., *Saccharomyces* spp.; and mold spp. including *Aspergillus* spp., *Penicillium* spp., and *Rhizopus* spp.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Figure 1:
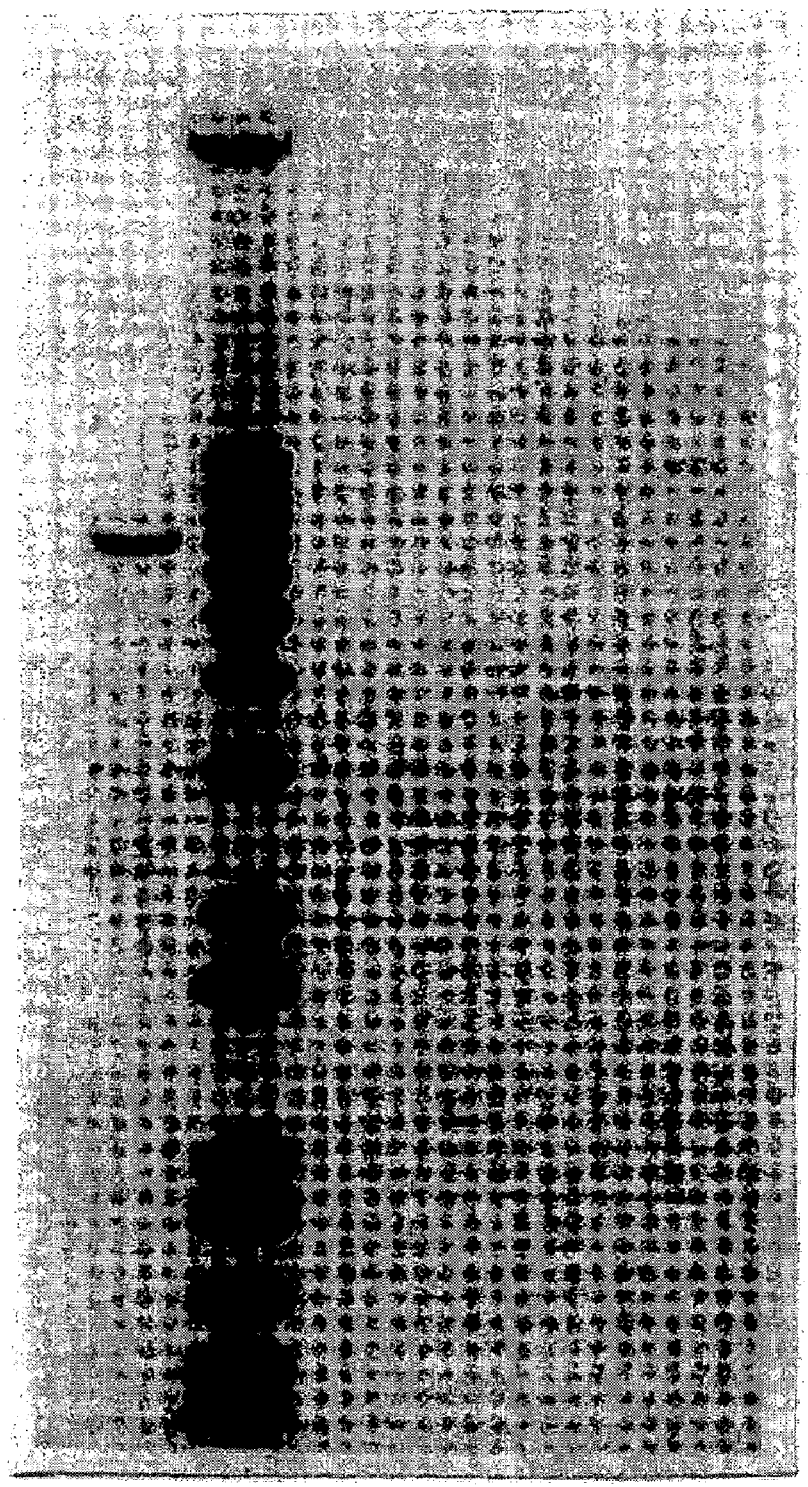
FIG. 1 is a photograph showing Southern blot analysis results of DNA fragments obtained by treating the genome of *Hansenula polymorpha* with BamHI (lane 3), EcoRI (lane 4), PstI (lane 5), and XbaI (lane 6), along with a EcoRI fragment of the *Saccharomyces cerevisiae* genome (lane 1) and a marker (lane 2) after the DNA fragments are hybridized with a SED1 gene as a probe.

Established in the present invention are systems for the export of exogenous polypeptides to discrete regions of a yeast cell in which it is expressed, which can be used for regenerable whole-cell biocatalyst.

To circumvent the problems associated with *Saccharomyces cerevisiae*, which has been used for the industrial production of recombinant proteins, *Hansenula polymorpha*, a methylotrophic yeast like *Pichia pastoris*, is studied for the expression of recombinant proteins. Because the cell wall structure of *Hansenula polymorpha* is not yet known, genes, which encode proteins mediating the exportation of exogenous proteins to the cell surface, are screened and cloned in the present invention. In addition, the cloned genes are fused to genes coding for proteins of interest to construct novel surface expression systems capable of expressing exogenous proteins on yeast cell surfaces.

Therefore, the present invention pertains to genes encoding cell wall proteins of *Hansenula polymorpha*.

Cell wall proteins of *Hansenula polymorpha* were identified to be very similar in characteristics to those of *Saccharomyces cerevisiae*. Genes coding for Cwp1p (GenBank D37975, van der Vaart et al., *J. Bacteriol.*, 1995, 177, 3104), Cwp2p (GenBank Z28096, Van der Vaart et al., *J. Bacteriol.*, 1995, 177, 3104), Sed1p (GenBank X66838, Seidel, J. and W. Tanner, *Yeast*, 1997, 13, 3104), Tir1p (GenBank X12775), and Tip1p (GenBank M71216, Van der Vaart et al., *J. Bacteriol.*, 1995, 177, 3104), all known as cell wall proteins, and Gas1p (GenBank X53424, Benghezal et al., *J. Cell Biol.*, 1995, 130, 1333) known as a cytoplasmic membrane protein, were used to search for corresponding ones from the genome of *Hansenula polymorpha*.

(1) Isolation of HpSED1 Gene of *Hansenula polymorpha*

Encoded by the gene SED1, 1,017 bp long, Sed1p is a protein which consists of 338 amino acid residues and a predominant protein on the cell wall of *Saccharomyces cerevisiae* in the stationary phase.

Using a SED1 gene segment of *S. cerevisiae* as a probe, a 4 kb EcoRI fragment was obtained from the genome of *Hansenula polymorpha* (see FIG. 1) and inserted into the vector. The SED1 homologous gene fragment of *Hansenula polymorpha* named as HpSED1, was identified to have the base sequence represented by the SEQ. ID. NO: 1, which codes for an open reading frame consisting of 131 amino acid residues represented by the SEQ. ID. NO: 11. This HpSED1 gene fragment of *Hansenula polymorpha* was much shorter than the SED1 gene of *S. cerevisiae*. However, the HpSed1p encoded by the HpSED1 gene of *Hansenula polymorpha* has the same amino acid repeating sequences, shows a similar threonine/serine-rich structure, and shares homology of 58.4% in amino acids sequence with *S. cerevisiae*. In addition, the HpSed1p of *Hansenula polymorpha* was seemed to have a signal sequence consisting of 17 amino acids, and a putative GPI-anchor signal at its carboxyl terminus. A novel *E. coli* transformant harboring a recombinant vector containing the 4 kb EcoRI fragment of the HpSED1 gene was deposited with the Korean Collection for Type Culture of Korea Research Institute of Bioscience and Biotechnology (KRIBB) under the accession No. KCTC 0825BP on Jul. 11, 2000.

(2) Isolation of HpPIR2 Gene of *Hansenula polymorpha*

Encoded by the TIR1 gene, 765 bp long, Tir1p is a protein found at the cell well of *S. cerevisiae*, consisting of 254 amino acids. The protein shows hyper N-glycosylation and is rich in serine/alanine and well expressed under the anaerobic condition.

Using a TIR1 gene fragment of *S. cerevisiae* as a probe, a 5 kb ClaI fragment was obtained from the genome of *Hansenula polymorpha* (see FIG. 2b) and inserted into a vector. DNA sequence analysis revealed that the ORF in the ClaI fragment shares homology of 51.2% with the PIR2 gene of *S. cerevisiae* (GenBank D13741, Toh-e et al., *Yeast*, 1993, 9, 481).

Cwp2p, consisting of 92 amino acids, is known as a most effective surface anchor except α-agglutinin, among the proteins of *S. cerevisiae* (van der Vaart et al., *Appl. Environ. Microbiol.*, 1997, 63, 615). In the present invention, a 5.5 kb SalI fragment obtained from the genome of *Hansenula polymorpha* using a *S. cerevisiae* CWP2 gene as a probe (see FIG. 2a), was identified as the same fragment with the ClaI fragment cloned by TIR1 by DNA sequencing. Both proteins, Cwp2p and Tir1p, were reported to contain the repeating amino acid sequences represented by the SEQ. ID. NO: 2, called PIR1/2/3 repeat which made strong homology with Pir2p protein.

The Pir2p of *S. cerevisiae* coded by PIR2 is known to be released from the cell wall by alkali treatment, usually have a Kex2 cleavage site, also this protein is anchored on the cell wall in a form different from that of the GPI (glycosylphosphatidylinositol)-anchor protein and is not released by glucanase treatment (Toh-e et al., *Yeast*, 1993, 9, 481). The N-terminal amino acids analysis of major cell wall protein released by alkali treatment from *Hansenula polymorpha* cell wall, showed the same amino acids sequence with the HpPir2p polypeptide following the kex2p cleavage site, represented by the SEQ. ID. NO: 3. Thus, the HpPIR2 gene obtained from *Hansenula polymorpha* was expected to be a gene coding for the HpPir2p, which located in the cell wall. The HpPir2p of *Hansenula polymorpha* is encoded by a 1,014 bp gene represented by the SEQ. ID. NO: 4, consisting of 337 amino acids with PIR1/2/3 repeat. This protein possessed a secretion signal sequence consisting of 18 amino acids and a Kex2p cleavage site at amino acid residue 68. A novel *E. coli* transformant harboring a recombinant vector containing the 5.5 kb SalI fragment of the HpPIR2 gene of *Hansenula polymorpha* was deposited with the Korean Collection for Type Culture of Korea Research Institute of Bioscience and Biotechnology (KRIBB) under the accession No. KCTC 0827BP on Jul. 11, 2000.

(3) Isolation of HpGAS1 Gene of *Hansenula polymorpha*

Encoded by the GAS1 gene, 1,680 bp long, Gas1p consists of 559 amino acids and is linked to the cell membrane of *Saccharomyces cerevisiae*. However, its amino terminal domain is exposed to the exterior, penetrating the cell wall.

In the present invention, using a GAS1 gene fragment of *S. cerevisiae* as a probe, a 3 kb PstI fragment was obtained from the genome of *Hansenula polymorpha* (see FIG. 3) and inserted into a vector. DNA sequence analysis revealed an ORF shares 70.7% homology with the Gas1p of *S. cerevisiae* and this was named as HpGas1p. HpGas1p of *Hansenula polymorpha* consists of 537 amino acids represented by the SEQ. ID. NO: 14, which is encoded by the gene represented by the SEQ. ID. NO: 5, 1,614 bp long. The Gas1p of *Hansenula polymorpha* also possesses a secretion signal sequence consisting of 18 amino acids, but GPI-anchor signal was different with that of *S. cerevisiae*. A novel *E. coli* transformant harboring a recombinant vector containing 3 kb PstI fragment of the HpGAS1 gene of *Hansenula polymorpha* was deposited with the Korean Collection for Type Culture of Korea Research Institute of Bioscience and Biotechnology (KRIBB) under the accession No. KCTC 0828BP on Jul. 11, 2000.

(4) Isolation of HpTIP1 Gene of *Hansenula polymorpha*

Encoded by the 633 bp, TIP1 gene of *Saccharomyces cerevisiae*, Tip1p is a GPI-anchor protein consisting of 210 amino acids with high homology with Tir1p and the expression of Tip1p is induced by cold shock.

In the present invention, using a TIP1 gene fragment of *S. cerevisiae* as a probe, a 3.5 kb XbaI fragment was obtained from the genome of *Hansenula polymorpha* (see FIG. 4) and inserted into a vector. DNA sequence analysis revealed an ORF consisting with 852 bp sequence represented by the SEQ. ID. NO: 6, coding for 283 amino acids represented by the SEQ. ID. NO: 13. A novel *E. coli* transformant harboring a recombinant vector containing the 3.5 kb XbaI fragment of the HpTIP1 gene of *Hansenula polymorpha* was deposited with the Korean Collection for Type Culture of Korea Research Institute of Bioscience and Biotechnology (KRIBB) under the accession No. KCTC 0824BP on Jul. 11, 2000.

(5) Isolation of HpCWP1 Gene of *Hansenula polymorpha*

Cwp1p is a typical GPI-anchor protein, which is encoded by the 720 bp, CWP1 gene of *Saccharomyces cerevisiae*, consisting of 239 amino acids.

In the present invention, using the full CWP1 gene of *S. cerevisiae*, a 6 kb SalI fragment was obtained from the genome of *Hansenula polymorpha* (see FIG. 5) and cloned into a vector. DNA sequence analysis revealed a putative ORF with 246 bp sequence represented by the SEQ. ID. NO: 7, which was named as HpCWP1, even though this protein showed low homology with the CWP1 of *S. cerevisiae*. Additionally, the HpCwp1p represented by the SEQ. ID. NO: 15, was deduced to have a secretion signal consisting of 15 amino acids, also the putative GPI-anchor signal. A novel *E. coli* transformant harboring a recombinant vector containing 6 kb SalI gene fragment coding for the HpCwp1p of *Hansenula polymorpha* was deposited with the Korean Collection for Type Culture of Korea Research Institute of Bioscience and Biotechnology (KRIBB) under the accession No. KCTC 0826BP on Jul. 11, 2000.

(6) Isolation of HpWSC1 Gene of *Hansenula polymorpha*

Wsc1p is a protein responsible for stress response, anchored in the cell membrane of *Saccharomyces cerevisiae*. This stress response protein was reported to have a carboxy-terminal transmembrane domain, a serine/threonine-rich domain traversing the cell wall, and an amino-terminal cystein motif which is exposed to the exterior, functioning to detect external signals (Verna et al., *Proc. Natl. Acad. Sci. USA*, 1997, 94, 13804).

Based on the fact that fluorescence was observed on the cell surface when a green fluorescence protein (GFP) was expressed as a fusion partner with Wsc1p, it was deduced that the amino terminal domain of Wsc1p could be used as a surface-expression mediator. In the process of isolating the *LEU2* gene of *Hansenula polymorpha*, the HpWSC1 gene was obtained by Agaphonov et al. (Agaphonov et al., *Yeast*, 1994, 10, 509, GenBank U00889). DNA sequencing analysis disclosed that the HpWSC1 gene of *Hansenula polymorpha* consists of the 1,110 bp sequence represented by the SEQ. ID. NO: 8 encoding the 373 amino acid sequence. The protein encoded by the HpWSC1 gene isolated from *Hansenula polymorpha* was assumed as a cell surface protein different in anchoring mechanism from GPI-anchor proteins and could be used to develop surface expression systems by fusion to the amino terminal domain of foreign proteins.

In accordance with the embodiment of the present invention, there are provided *Hansenula polymorpha*-derived cell wall protein genes, HpSED1, HpPIR2, HpGAS1, HpTIP1, and HpCWP1, and a membrane protein gene HpWSC1 gene, vectors containing them, and cells transformed with the vectors.

Also, the present invention pertains to surface expression systems using novel cell wall proteins isolated from *Hansenula polymorpha* as mediators for surface expression of foreign proteins.

In accordance with another embodiment of the present invention, there are provided surface expression systems using GPI-anchor proteins isolated from *Hansenula polymorpha*, as mediators for surface expression of foreign proteins.

Expected to be useful as mediator genes for surface expression systems, four putative GPI-anchor protein genes are cloned from *Hansenula polymorpha*. Along with each of the mediators, carboxyl methyl cellulase (hereinafter referred to as "CMCase") derived from *Bacillus subtilis* (Park et al., *Agric. Biol. Chem.*, 1991, 55, 441) is used in the surface expression systems as a reporter protein, in accordance with the present invention.

In this regard, a GAPDH promoter (Sohn et al., *Appl. Microbiol. Biotechnol.*, 1999, 51, 800) and a killer toxin signal sequence (Sor, F. and Fukuhara, *Curr. Genet.*, 1985, 9, 147) were inserted into an expression vector. Then, the CMCase gene was fused in frame to construct a CMCase surface expression vector, which can express CMCase under the control of the GAPDH promoter. Four putative GPI-anchor protein genes, HpCWP1, HpGAS1, HpTIP1 and HpSED1 gene fragments, are individually inserted to the expression vector at a carboxy terminal region of the CMCase to construct a CMCase surface expression vector. Based on the fact that a GPI-anchor motif located within the 40 amino acids of carboxy terminus (van der Vaart et al., *Appl. Environ. Microbiol.*, 1997, 63, 615), CMCase surface expression vectors were also constructed with a nucleic acid segment encoding the carboxy-terminal 40 amino acids of each mediators. After all of the surface expression vectors were introduced to *Hansenula polymorpha* (Hill et al., *Nucl. Acids Res.*, 1991, 19, 5791), the transformants thus obtained were cultured and the CMCase activity of them was measured in the supernatant and the whole cell fraction.

In whole cell fractions, the expression vectors in which each of the mediator genes was inserted exhibit significantly improved CMCase activity compared to control vectors in which the signal sequence is absent or no mediator genes are fused, demonstrating that CMCase is exported to the cell surface by each mediator (see Table 1). Especially, HpTip1p, HpGas1p and HpCwp1p were found to translocate CMCase to the cell surface at higher efficiency than other mediators (see FIG. 7).

While the CMCase activity was decreased in most of the cells when they reached the stationary phase, the CMCase activity of the cells using HpCwp1p as a surface anchor were found to remain high throughout the culturing period, although being lowered in the stationary phase. Therefore, HpCwp1p was inferred to be the most stable mediator among the proteins tested (see FIG. 8).

In accordance with a further embodiment of the present invention, there are provided surface expression systems using non GPI-anchor proteins isolated from *Hansenula polymorpha* as mediators for surface expression of foreign proteins.

In one version of this embodiment, an HpPIR2 gene, which encodes a cell wall protein different from GPI-anchor proteins were used for constructing a surface expression system.

In contrast to GPI-anchor proteins, the protein Pir2p is anchored in the cell wall through the hyper O-glycosylation of its serine/threonine-rich domain with the glycans present in the cell wall. Thus, the protein Pir2p is not released from the cell wall by the enzymes, which hydrolyze glycans only, but released from the cell wall by alkaline treatment, which cleaves all glycosylation. In the present invention, surface expression systems utilizing carboxy- and amino-terminal regions of the protein HpPir2p were constructed. To evaluate the anchoring ability of the mediators derived from HpPir2p, CMCase, the reporter, activity was measured (see FIG. 9).

Almost the same CMCase activity was obtained when the carboxy-terminal region of the protein HpPir2p was expressed as a mediator as when CMCase gene without mediator was expressed. By contrast, where the amino-terminal region of the protein HpPir2p was used as an anchoring mediator, CMCase activity was detected not only in the supernatant, but also in the whole cell fraction (see Table 2). It was reported that the protein Pir2p was secreted to the culture medium by the overexpression thereof in vivo (Russo et al., *Proc. Natl. Acad. Sci. USA*, 1992, 89, 3671). Therefore, the CMCase activity detected in the whole cell fraction was attributed by the enzyme anchored in the cell wall.

Therefore, the protein HpPir2p can be anchored in the cell wall and be used as a surface expression mediator. Over conventional GPI-anchor proteins, the protein Pir2p has the advantage of linking to an amino terminal of target protein to its carboxy terminus.

In another version of the embodiment, the WSC1 gene, which encodes a transmembrane protein different from GPI-anchor proteins, was used to construct a surface expression system.

Figure 10A:
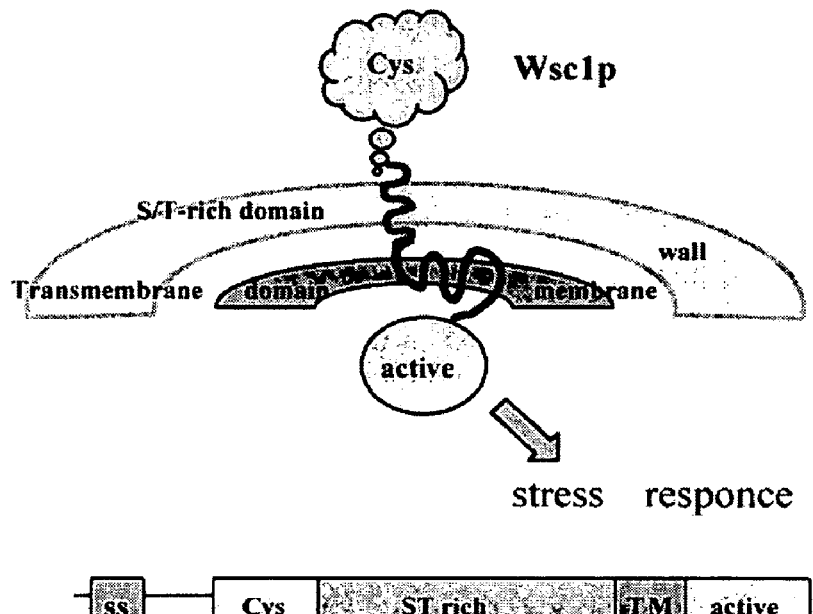
FIG. 10a is a schematic diagram showing domains of the protein Wsc1p and their cellular location sites.

The protein Wsc1p is composed of a transmembrane domain by which the protein is anchored in the cell membrane, a serine/threonine-rich domain that traverses the cell wall, and an amino-terminal cystein motif which exists in the extracellular space (Verna et al., *Proc. Natl. Sci. USA*, 1997, 13804), as illustrated in FIG. 10a.

Figure 10B:
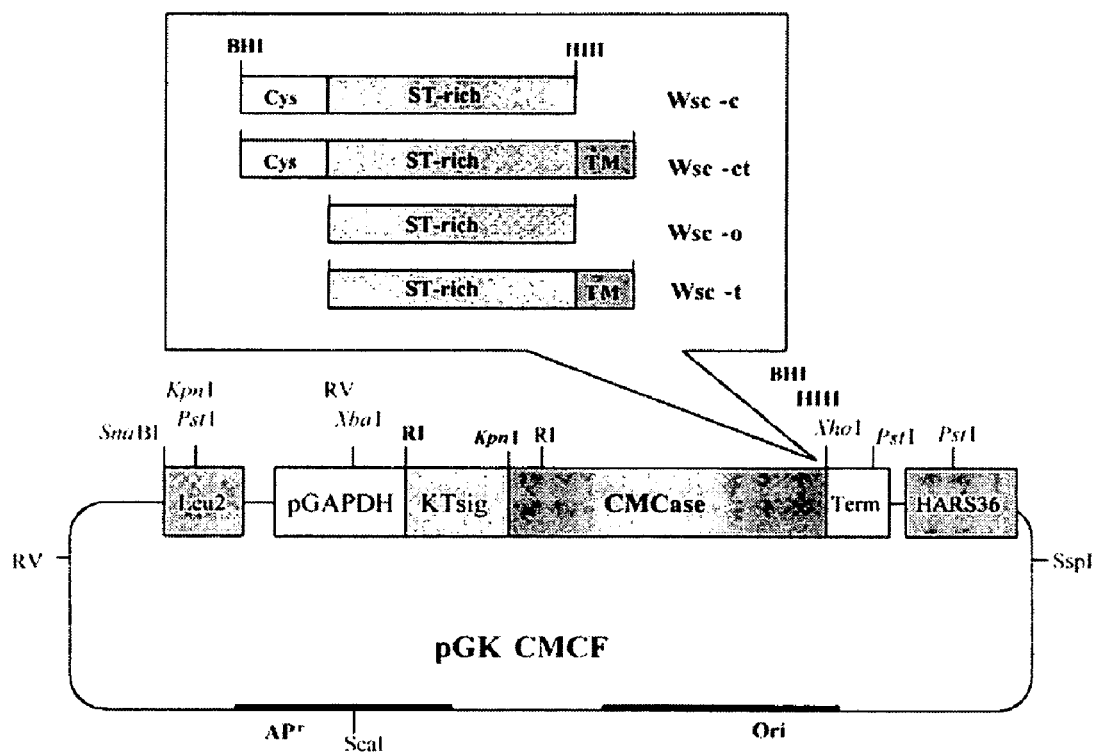
FIG. 10b is a schematic diagram showing surface expression vectors for expressing exogenous proteins on the cell surface of *Hansenula polymorpha*, in which several truncated HpWSC1 gene fragments, devoid of either the cystein motif or the transmembrane domain, and of both of them, and an intact HpWSC1 gene encoding the full length of HpWsc1p, are inserted.

In order to establish a surface expression system using the HpWsc1p, several truncated HpWSC1 gene fragments, devoid of either the cystein motif or the transmembrane domain and of both of them were inserted in the CMCase expression vector (see FIG. 10b) and the CMCase activity was analyzed.

Only where the transmembrane domain was presented in the fusion protein, the CMCase was not secreted, but rather attached to the cell. However, although the transmembrane domain was present, CMCase activity was not detected in the whole cell fraction unless the cystein motif is present. This result might come from the fact that the CMCase was not sufficiently exposed on the cell surface. In contrast, where the transmembrane domain was absent, the CMCase activity was mostly detected in the supernatant. In addition, the cystein motif made an additional contribution to the secretion of the CMCase (see Table 3).

Therefore, the mediator derived from the HpWsc1p must have the cystein motif and the transmembrane domain, both, for anchoring efficiency. In the present invention, the HpWsc1p was suggested as a novel mediator for surface expression of proteins.

In accordance with still a further embodiment of the present invention, there are provided surface expression systems for exporting glucose oxidase to the cell surface by use of the HpTip1p, HpGas1p and HpCwp1p, and the HpWsc1p.

Glucose oxidase, a flavoenzyme derived from *Aspergillus niger*, consists of two identical polypeptide chain subunits. Upon being expressed in *Hansenula polymorpha*, this enzyme is known to undergo hyper glycosylation.

Figure 11:
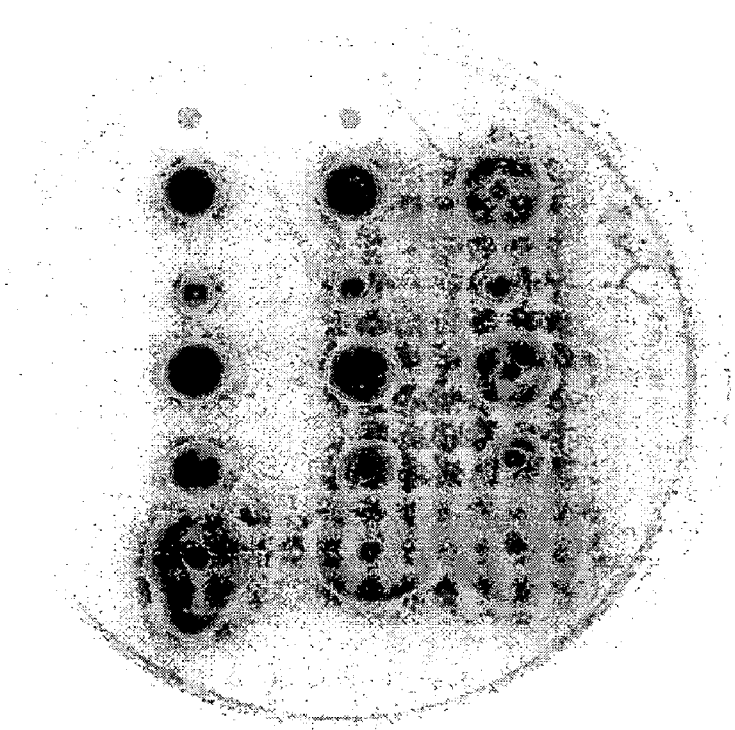
FIG. 11 is a photograph showing the glucose oxidase activity measured according to the plate activity assay method from *Hansenula polymorpha* strains which use expression mediators (Tip40, GasF, CwpF and Wsc-ct) and no expression mediators (GOD*).

When being expressed in the presence of the anchoring mediators such as HpTip1p, HpGas1p, HpCwp1p and HpWsc1p, glucose oxidase was found to form smaller activity circles on plates (Hodgkins et al., *Yeast*, 1993, 9, 625) than the secreted ones (see FIG. 11).

In all cases of using the anchoring mediators, fluorescent cells were observed by FACS (fluorescence activated cell sorter) analysis, indicating that the glucose oxidase was expressed and anchored onto the cell surface. Additionally, higher glucose oxidase activity was detected in the whole cell fraction than in the supernatant throughout all of strains. When HpCwp1p was employed, fluorescence was detected from a large number of cells, demonstrating that HpCwp1p had an excellent cell wall anchoring activity. It was also found that the 40 amino acids fragment of HpTip1p was efficient in expression of proteins onto the cell surface (see FIG. 12). Under the mediation of HpGas1p and HpWsc1p, fluorescence, which proves the cell wall anchoring activity, was detected, but in a low level. However, even in this case, there seemed to be no problems in detecting the activity of the enzyme if the substrate penetrated the cell wall.

Accordingly, not only is HpCwp1p found to be the most effective surface expression mediator among the GPI-anchor proteins, but also the proteins HpPir2p and HpWsc1p can be suggested as novel expression mediators in accordance with the present invention.

Herein, useful in the present invention is a eukaryotic cell selected from the group consisting of yeast spp., including *Candida* spp., *Debaryomyces* spp., *Hansenula* spp., *Kluyveromyces* spp., *Pichia* spp., *Schizosaccharomyces* spp., *Yarrowia* spp., *Saccharomyces* spp.; and mold spp. including *Aspergillus* spp., *Penicillium* spp., and *Rhizopus* spp.

In accordance with still another embodiment of the present invention, there are provided surface expression systems using the *Saccharomyces diastaticus*-derived glucoamylase gene STA1.

With the 2,337 bp sequence represented by the SEQ. ID. No: 9, the glucoamylase derived from *Saccharomyces diastaticus* is secreted to extracellular spaces to hydrolyze extracellular starch. The amino acid sequence analysis of this enzyme showed a signal sequence (SS) in the amino-terminal region and threonine/serine-rich (TS-rich) domain which containing the threonine and serine residues in an amount of 55% of the total amino acid residues. The signal sequence and the threonine/serine-rich domain are linked to each other via the octapeptide represented by the SEQ. ID. NO: 10. While this octapeptide plays a role in directing the protein to the exterior, the threonine/serine-rich domain is responsible for the support of the proteins upon its penetration through the cell wall, thus acting like an anchoring mediator (Venturini et al., *Mol. Microbiol.*, 1997, 23, 997; Yamashita, I., *Agric. Biol. Chem.*, 1989, 53, 483; Yamashita et al., *Agric. Biol. Chem.*, 1984, 48, 1611).

Figure 13:
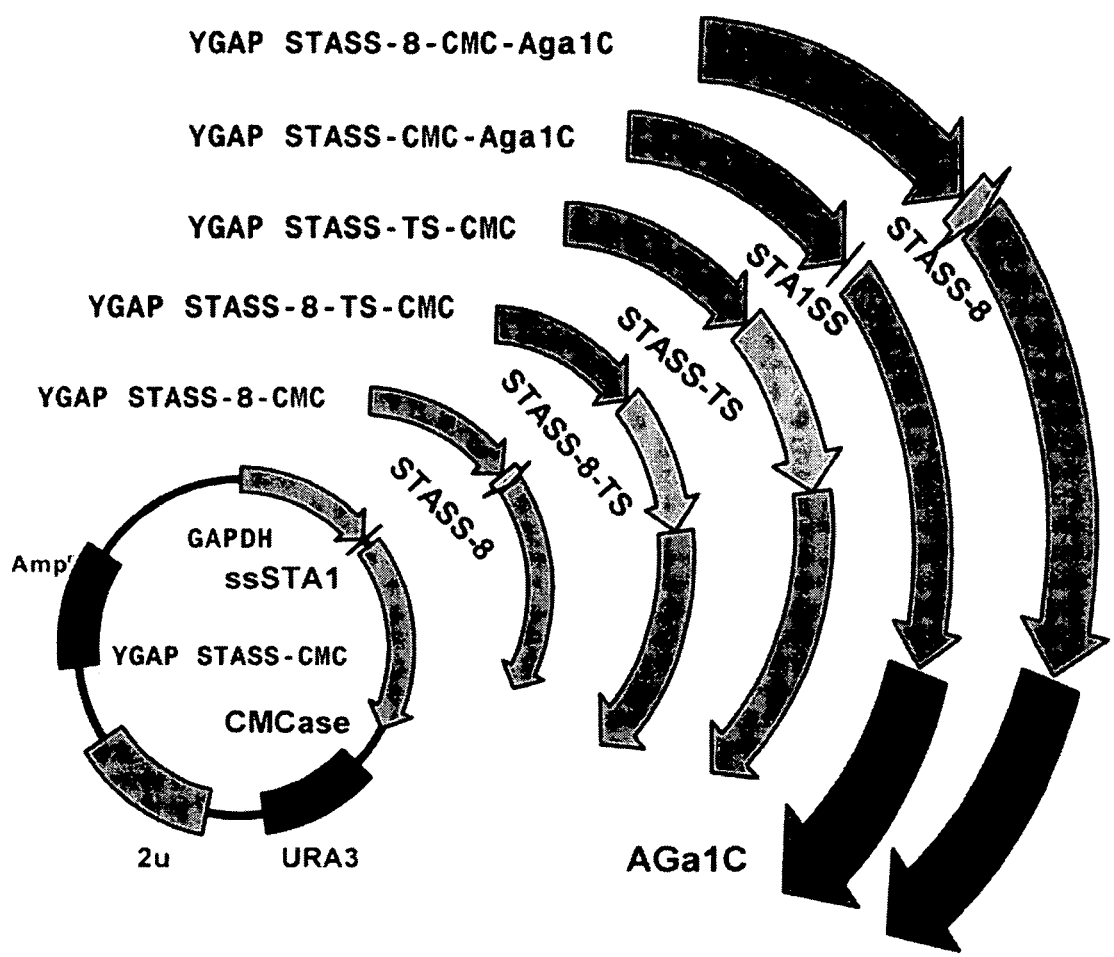
FIG. 13 is a schematic diagram showing surface expression systems for expressing exogenous proteins on the cell surface of *Saccharomyces cerevisiae* by use of the gene STA1, which are constructed with vectors comprising the signal sequence only (STASS), both of the signal sequence and the octapeptide sequence (STASS-8), all of the signal sequence, the octapeptide sequence and the threonine/serine-rich domain (STASS-8-TS), both of the signal sequence and the threonine/serine-rich domain (STASS-TS), both of the signal sequence and alpha-agglutinin (STASS-CMC-Agalc), and all of the signal sequence, the octapeptide, and alpha-agglutinin (STASS-8-CMC-Agalc), along with a CMCase gene as a reporter gene.

With reference to FIG. 13, there are shown vector diagrams for the surface expression systems using the STA1 gene. As depicted, the surface expression systems are constructed with vectors containing the signal sequence only, both of the signal sequence and the octapeptide sequence, all of the signal sequence, the octapeptide sequence and the threonine/serine-rich domain, both of the signal sequence and alpha-agglutinin, and all of the signal sequence, the octapeptide, and alpha-agglutinin, along with a CMCase gene as a reporter gene.

When employing the signal sequence only, most of the CMCase was secreted extracellularly, not anchored in the cell wall, as measured by the pNPC (p-nitrophenyl β-D-cellobiocide) method (Deshpande et al., *Anal. Biochem.*, 1984, 138, 481). In contrast, when employing the threonine/serine-rich domain linked to the signal sequence via the octapeptide sequence, the CMCase activity was low in the supernatant, but high in the whole cell fraction. The same results were confirmed by plate activity assay. Large circles were formed around the colonies, which harbor the signal sequence only, indicating that the CMCase was mostly secreted outside the cells. The presence of the threonine/serine-rich domain hindered the enzyme secretion, as proven by the small circles formed around the colonies (see Table 4 and FIG. 14).

Figure 15:
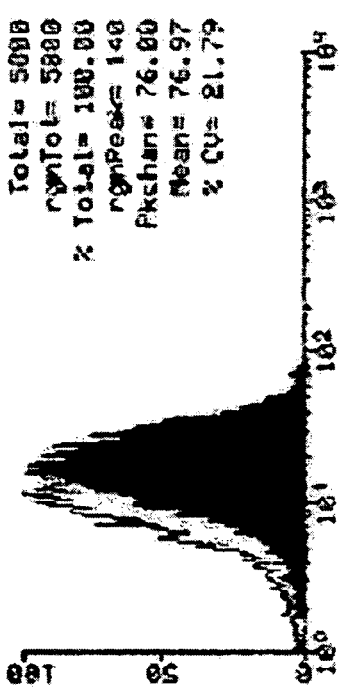
FIG. 15 shows FACS analysis results of *Saccharomyces cerevisiae* strains on which CMCase is expressed by employing surface expression vectors (gray), along with a wild type (white).
Figure 15:
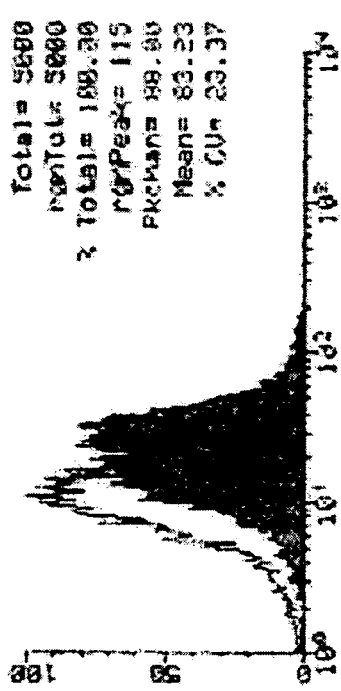
Figure 15:
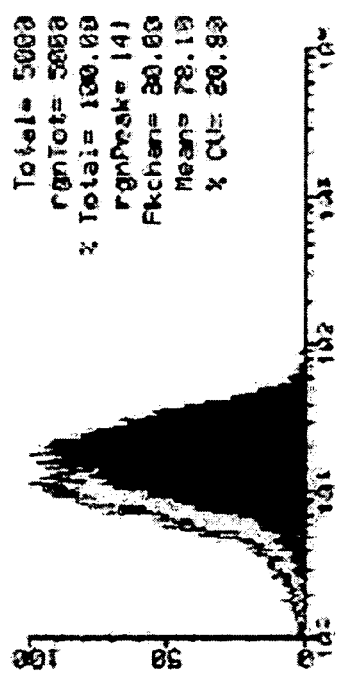
Figure 15:
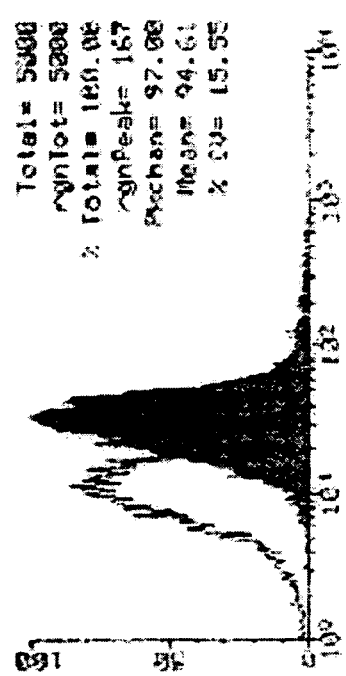

In addition, fluorescence was detected in the cells harboring the threonine/serine-rich domain by FACS analysis, suggesting the presence of CMCase on the cell surface (see FIG. 15).

When glucoamylase gene was used for the construction of surface expression systems, glucoamylase or its domains could be fused to the amino terminus of target protein. Thus, these systems could circumvent the problems arising when a carboxy-terminal active domain of the target protein was interrupted by the mediator fused to the carboxy terminus.

Therefore, the mediators described herein allow the development of surface expression systems capable of expressing various types of target proteins, according to the characteristics of the target proteins.

EXAMPLES

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Isolation of Genes Encoding Cell Wall Expression Proteins from *Hansenula polymorpha*

For use in the cloning, the strain DL1-L (Δ leu2), derived from *Hansenula polymorpha* DL1 (ATCC 26012) was obtained from NPO Biotechnologia (Moscow, Russia). Cell wall protein profile analysis by biotin labeling, which cannot penetrate into the cell wall, demonstrated that this strain had very similar profile of surface proteins with *Saccharomyces cerevisiae*. For the cloning of cell wall protein genes from *Hansenula polymorpha*, the genes encoding the glucanase extractable cell wall proteins of *S. cerevisiae* were utilized.

In order to isolate the cell wall protein gene from *Hansenula polymorpha*, genes coding for Cwp1p (GenBank D37975, van der Vaart et al., *J. Bacteriol.*, 1995, 177, 3104), Cwp2p (GenBank Z28096, van der Vaart et al., *J. Bacteriol.*, 1995, 177, 3104), Sed1p (GenBank X66838, Seidel, J. and W. Tanner, *Yeast*, 1997, 13, 3104), Tir1p (GenBank X12775), and Tip1p (GenBank M71216, van der Vaart et al., *J. Bacteriol.*, 1995, 177, 3104), all known as cell wall expression proteins, and Gas1p (GenBank X53424, Benghezal et al., *J. Cell Biol.*, 1995, 130, 1333) known as a cytoplasmic membrane protein, were obtained from *S. cerevisiae*. Reportedly, these proteins can be separated from the cell wall by glucanase treatment because their carboxy termini are linked to β-1,6-glucan of the cell wall via GPI-anchor (Kapteyn et al., *Biochim. Biophys. Act.*, 1999, 1426, 373; Kolla et al., *J. Biol. Chem.*, 1997, 272, 17762). Using these genes as probes, the genome of *Hansenula polymorpha* was subjected to southern blot analysis. No clear signals were obtained from the genomic DNA of *Hansenula polymorpha* when the Cwp1p gene of *S. cerevisiae* was used as a probe. This was inferred to result from low homology of the gene between the two strains. In the cases of the other four genes, clear signals were observed. From the genomic library, corresponding DNA fragments were cloned.

<1-1> Isolation of HpSED1 Gene of *Hansenula polymorpha*

In order to isolate the SED1 homologue from *Hansenula polymorpha*, the open reading frame of the *Saccharomyces cerevisiae* SED1 gene was labeled according to the Klenow fragment method by a DIG labeling system (Boehringer Mannheim) and this was used as a probe for Southern blot analysis. Following hybridization at 42° C. in a 30% formamide solution, signal was detected.

The southern blot analysis results are given in FIG. 1. From the EcoRI fragment, a signal was detected at a size of about 4 kb. After the elution of DNA around 4 kb from the gel, the DNA fragment was inserted to pBluescript II SK(+) at a EcoRI site to construct a library. Under the same condition, southern blot analysis was conducted with the library to obtain a recombinant vector in which a DNA fragment hybridized with the probe was inserted. The DNA sequence analysis of the recombinant vector, named HpSED1, revealed that the 4 kb DNA fragment has a base sequence represented by the SEQ. ID. NO: 1 with an open reading frame consisting of 131 amino acids represented by the SEQ. ID. NO: 11. The HpSED1 gene of *Hansenula polymorpha* was found to be far shorter than, but have the same amino acid repeating sequences as the corresponding gene of *S. cerevisiae* and show a similar threonine/serine-rich structure, sharing homology of 58.4% with Sed1p of *S. cerevisiae*. In addition, the HpSed1p of *Hansenula polymorpha* was expected to have a signal sequence consisting of 17 amino acids, and a GPI-anchor signal at its carboxyl terminus, as analyzed by the PSORT II prediction program. A novel *E. coli* transformant harboring a recombinant vector in which the 4 kb EcoR1 fragment containing the HpSED1 gene of *Hansenula polymorpha* is inserted, was deposited with the Korean Collection for Type Culture of Korea Research Institute of Bioscience and Biotechnology (KRIBB) under the accession No. KCTC 0825BP on Jul. 11, 2000.

<1-2> Isolation of HpPIR2 Gene of *Hansenula polymorpha*

In order to isolate the TIR1 homologue from *Hansenula polymorpha*, the open reading frame of the *Saccharomyces cerevisiae* TIR1 gene was labeled according to the Klenow fragment method by a DIG labeling system (Boehringer Mannheim) and this fragment was used as a probe for southern blot analysis. Following hybridization at 42° C. in a 30% formamide solution, signal was detected.

Figure 2A:
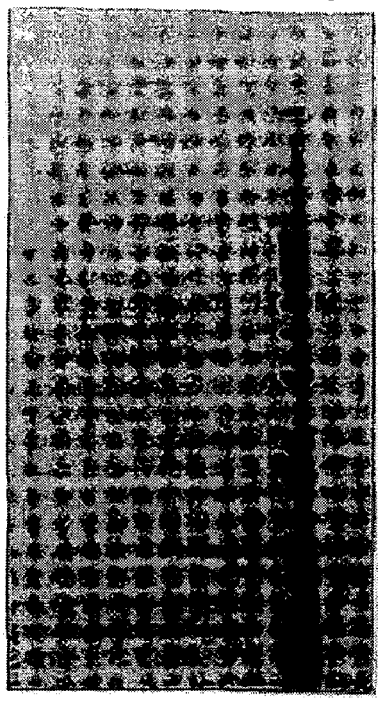
FIG. 2*a* is a photograph showing Southern blot analysis results of DNA fragments obtained by treating the genome of *Hansenula polymorpha* with ClaI (lane 1), EcoRI (lane 2), HindIII (lane 3), SalI (lane 4) and XhoI (lane 6), along with a marker (lane 6) and an EcoRI fragment of the *Saccharomyces cerevisiae* (lane 7) after the DNA fragments are hybridized with a CWP2 gene as a probe.
Figure 2B:
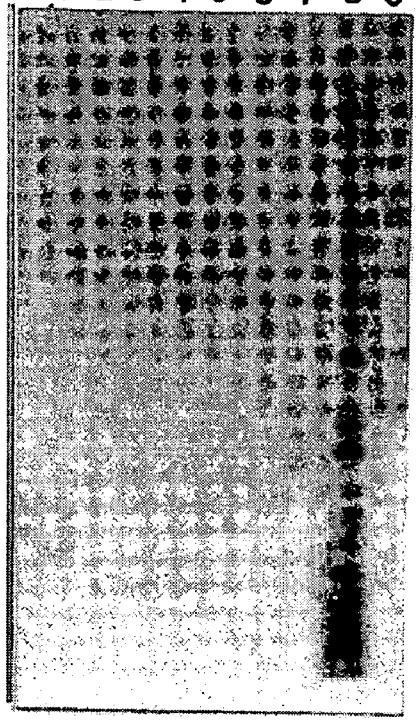
FIG. 2*b* is a photograph showing Southern blot analysis results of DNA fragments obtained by treating the genome of *Hansenula polymorpha* with BamHI (lane 1), ClaI (lane 2), EcoRI (lane 3), HindIII (lane 4), PstI (lane 5), XbaI (lane 6), and XhoI (lane 7), along with a marker (lane 8) and an EcoRI fragment of *Saccharomyces cerevisiae* genome after the DNA fragments are hybridized with a TIR1 gene as a probe.

The southern blot analysis results are given in FIG. 2b. From the ClaI digested fragment, a signal was detected at about 5 kb (lane 9). After the elution of this part from the gel, the DNA fragment was inserted to pBluescript II SK(+) at a ClaI site to construct a recombinant vector library. Using the same method as <1-1>, a recombinant vector containing a 5 kb ClaI DNA fragment hybridized with the probe was obtained. The DNA sequence analysis of this 5 kb ClaI DNA fragment, revealed an ORF that the shares homology of 51.2% with the Pir2p of *S. cerevisiae*.

To clone the CWP2 homologue from *H. polymorpha*, the open reading frame of the *S. cerevisiae* CWP2 gene was labeled according to the Klenow fragment method by a DIG labeling system and used as a probe. Southern hybridization was conducted at 42° C. in a 30% formamide solution to detect signals. The southern blot analysis results are shown in FIG. 2a. From a 5.5 kb SalI fragment, an apparent signal was detected. This 5.5 kb SalI fragment was identified to have the same DNA sequence with the ClaI fragment, as analyzed by DNA sequencing. Both of the proteins, Cwp2p and Tir1p, were found to contain the repeating amino acid sequence represented by the SEQ. ID. NO: 2, called PIR1/2/3 repeat. It was inferred that these repeating sequences might share high homology with the HpPIR2 gene of *Hansenula polymorpha*, thus resulting in the hybridization of the HpPIR2 gene with the probe. To exclude this possibility, each gene deprived of the repeating sequences was used as a probe for southern blot analysis, but no clear signals were observed.

Encoded by the PIR2 gene isolated from *S. cerevisiae*, the Pir2p protein was reported to be released from the cell wall by alkali treatment and not released by glucanase treatment, which meant that this protein anchored onto the cell wall in a different form from that of the GPI (glycosyl-phosphatidylinositol)-anchor protein, also it was known that this protein had a Kex2 cleavage site (Toh-e et al., Yeast, 1993, 9, 481). The N-terminal amino acids analysis of major cell wall protein released by by 30 mM sodium hydroxide (NaOH) from *Hansenula polymorpha* cell wall (Mrsa et al., Yeast, 13, 1145–1154, 1997), showed the same amino acids sequence with the HpPir2p polypeptide following the kex2 cleavage site, represented by the SEQ. ID. NO: 3. Thus, the gene HpPIR2 obtained from *Hansenula polymorpha* was inferred to code for the protein HpPir2p, which translocates to the cell wall.

The Pir2p protein of *Hansenula polymorpha* was encoded by a 1,014 bp gene, represented by the SEQ. ID. NO: 4, consisting of 337 amino acids with PIR1/2/3 repeats, represented by the SEQ. ID. NO:12. This protein possesses a secretion signal sequence consisting of 18 amino acids and a Kex2 cleavage site at amino acid residue 68. A novel *E. coli* transformant transformed with a recombinant vector in which the 5.5 kb SalI fragment of the HpPIR2 gene of *Hansenula polymorpha* is inserted was deposited with the Korean Collection for Type Culture of Korea Research Institute of Bioscience and Biotechnology (KRIBB) under the accession No. KCTC 0827BP on Jul. 11, 2000.

<1-3> Isolation of HpGAS1 Gene of *Hansenula polymorpha*

*S. cerevisiae* GAS1 gene was labeled by the Klenow fragment method with the aid of a DIG labeling system (Boehringer Mannheim) and used as a probe for southern blot analysis. Following hybridization at 42° C. in a 30% formamide solution, signal was detected.

Figure 3:
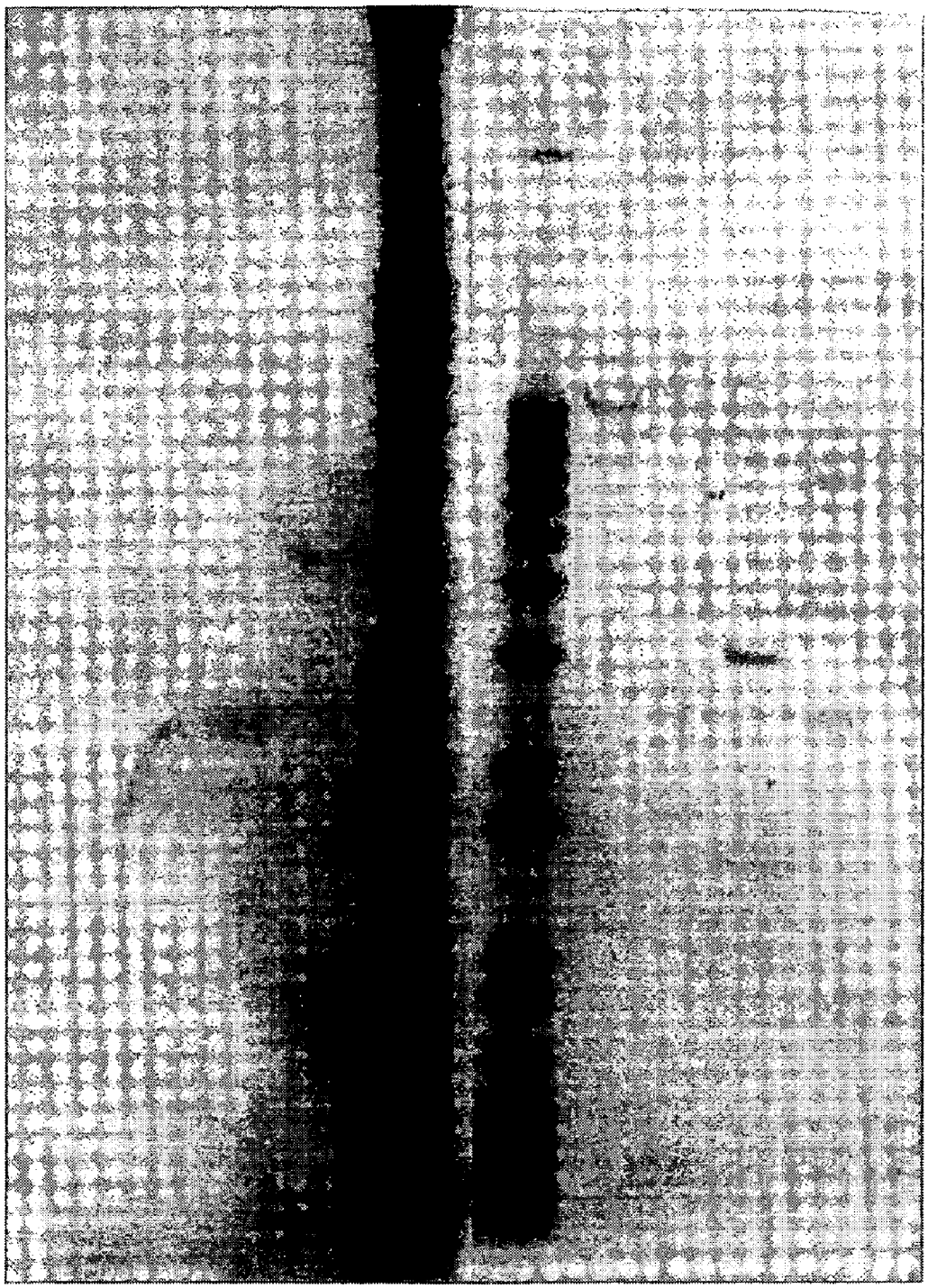
FIG. 3 is a photograph showing Southern blot analysis results of DNA fragments obtained by treating the genome of *Hansenula polymorpha* with ClaI (lane 1), HindIII (lane 2), SalI (lane 3), XhoI (lane 4), BamHI (lane 7), EcoRI (lane 8), PstI (lane 9), and XbaI (lane 10), along with a marker (lane 5 and 6), after the DNA fragments are hybridized with a GAS1 gene as a probe.

From the SalI fragment, a signal was detected at a size of about 1.6 kb. To identify the full length of the gene, the genome was treated with other restriction enzyme and hybridized with the same probe at 42° C. in 20% formamide. As shown in FIG. 3, a signal was detected at a 3 kb PstI fragment. This PstI fragment was cloned and inserted to pBluescript II SK(+) at a PstI site to construct a recombinant vector, named HpGAS1. The DNA sequence analysis of the recombinant vector revealed that the HpGas1p of *Hansenula polymorpha*, encoded by the gene represented by the SEQ. ID. NO: 5, 1,614 bp long, consisted of 537 amino acids represented by the SEQ. ID. NO: 14, and shared homology of as high as 70.7% with the Gas1p of *S. cerevisiae*. The HpGas1p of *Hansenula polymorpha* was also found to possess a secretion signal sequence consisting of 18 amino acids, but GPI-anchor signal was different with that of *S. cerevisiae*.

A novel *E. coli* transformant harboring a recombinant vector in which the 3 kb PstI fragment containing HpGAS1 gene of *Hansenula polymorpha* was deposited with the Korean Collection for Type Culture of Korea Research Institute of Bioscience and Biotechnology (KRIBB) under the accession No. KCTC 0828BP on Jul. 11, 2000.

<1-4> Isolation of HpTIP1 Gene of *Hansenula polymorpha*

The open reading frame of the *Saccharomyces cerevisiae* TIP1 gene was labeled according to the Klenow fragment method by a DIG labeling system (Boehringer Mannheim) and used as a probe for southern blot analysis for screening the TIP1 homologue from *Hansenula polymorpha*. Following hybridization at 42° C. in a 30% formamide solution, southern blot signal was detected.

Figure 4:
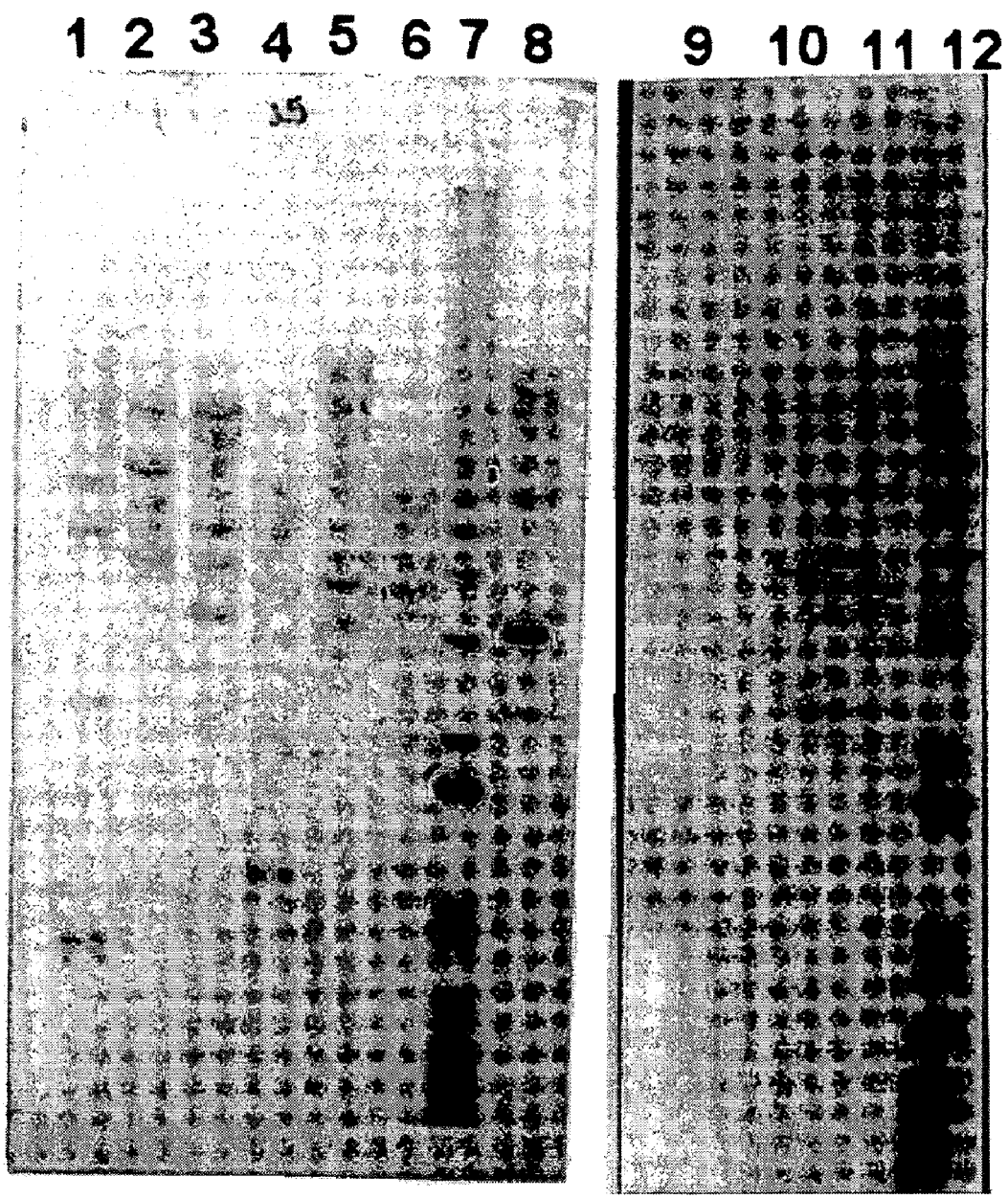
FIG. 4 is a photograph showing Southern blot analysis results of DNA fragments obtained by treating the genome of *Hansenula polymorpha* with BamH1 (lane 1), EcoRI (lane 2), ClaI (lane 3), PstI (lane 4), XbaI (lane 5), XhoI (lane 6), EcoRI (lane 9), XbaI (lane 10), XhoI (lane 11), along with a marker (lanes 7 and 12) and an EcoRI fragment of the *Saccharomyces cerevisiae* genome (lane 8), after the DNA fragments are hybridized with a TIP1 gene as a probe.

The southern blot analysis results are given in FIG. 4. At a 3.5 kb XbaI fragment, an apparent signal was detected. This 3.5 kb fragment was inserted to pBluescript II SK(+) at a XbaI site to construct a recombinant vector, named HpTIP1. The DNA sequence analysis of the recombinant vector revealed that the cloned gene had an 852 bp sequence represented by the SEQ. ID. NO: 6, coding for 283 amino acids represented by the SEQ. ID. NO: 13. A novel *E. coli* transformant harboring a recombinant vector containing the 3.5 kb XbaI fragment of the HpTIP1 gene was deposited with the Korean Collection for Type Culture of Korea Research Institute of Bioscience and Biotechnology (KRIBB) under the accession No. KCTC 0824BP on Jul. 11, 2000.

<1-5> Isolation of HpCWP1 Gene of *Hansenula polymorpha*

The open reading frame of the *Saccharomyces cerevisiae* CWP1 gene was labeled according to the Klenow fragment method by a DIG labeling system (Boehringer Mannheim) and used as a probe for Southern blot analysis for screening the CWP1 homologue from *Hansenula polymorpha*. Following hybridization at 42° C. in a 30% formamide solution, southern blot signal was detected.

Figure 5:
FIG. 5 is a photograph showing Southern blot analysis results of DNA fragments obtained by treating the genome of *Hansenula polymorpha* with ClaI (lane 1), HindIII (lane 2), PstI (lane 3), SalI (lane 4), and XhoI (lane 5), after the DNA fragments are hybridized with a CWP1 gene as a probe.

As shown in FIG. 5, several weak signals were detected. Among the various signals, a 6 kb SalI fragment showing the most clear signal was cloned into pBluescript II SK(+) at a SalI site to construct a recombinant vector, named HpCWP1. DNA sequence analysis disclosed that the cloned gene in the recombinant vector has a 246 bp sequences, which is expected to be an open reading frame represented by the SEQ. ID. NO: 7 with very low homology with the Cwp1p of *S. cerevisiae*. Additionally, the amino acid sequence, represented by the SEQ. ID. NO: 15, was expected to have a secretion signal consisting of 15 amino acids and a GPI-anchor signal predicted by the POSRT II prediction program. The corresponding protein was named HpCwp1p. It was expected to be a cell wall protein by its amino acids structure. A novel *E. coli* transformant harboring a recombinant vector containing the 6 kb SalI fragment coding for the HpCwp1p of *Hansenula polymorpha* was deposited with the Korean Collection for Type Culture of Korea Research Institute of Bioscience and Biotechnology (KRIBB) under the accession No. KCTC 0826BP on Jul. 11, 2000.

<1-6> Isolation of HpWSC1 Gene of *Hansenula polymorpha*

Based on the fact that fluorescence was observed on the cell surface when a green fluorescence protein (GFP) was expressed as a fusion partner with Wsc1p, it was deduced that the amino terminal domain of Wsc1p could be used as a surface-expression mediator.

In the process of isolating the LEU2 gene of *Hansenula polymorpha*, the HpWSC1 gene was obtained by Agaphonov et al. (Agaphonov et al., *Yeast*, 1994, 10, 509, GenBank U00889). DNA sequencing analysis disclosed that the HpWSC1 gene of *Hansenula polymorpha* consists of the 1,110 bp sequence represented by the SEQ. ID. NO: 8 encoding a 373 amino acid sequence. The protein encoded by the HpWSC1 gene isolated from *Hansenula polymorpha* is a cell surface protein different in anchoring mechanism from GPI-anchor proteins and can be used to develop surface expression systems by its amino terminal domain.

Example 2

Surface Expression System Using Cell Wall Proteins Isolated from *Hansenula polymorpha*

<2-1> Construction of Surface Expression System

Surface expression systems were constructed in which the four GPI-anchor protein genes and the HpWSC1 gene, isolated from *Hansenula polymorpha* in Example 1, were used as mediator genes for surface expression of foreign proteins. Together with each mediator gene, a CMCase gene derived from *Bacillus subtilis* (Park et al., *Agric. Biol. Chem.*, 1991, 55, 441) was used in the surface expression systems, functioning as a reporter gene.

Figure 6:
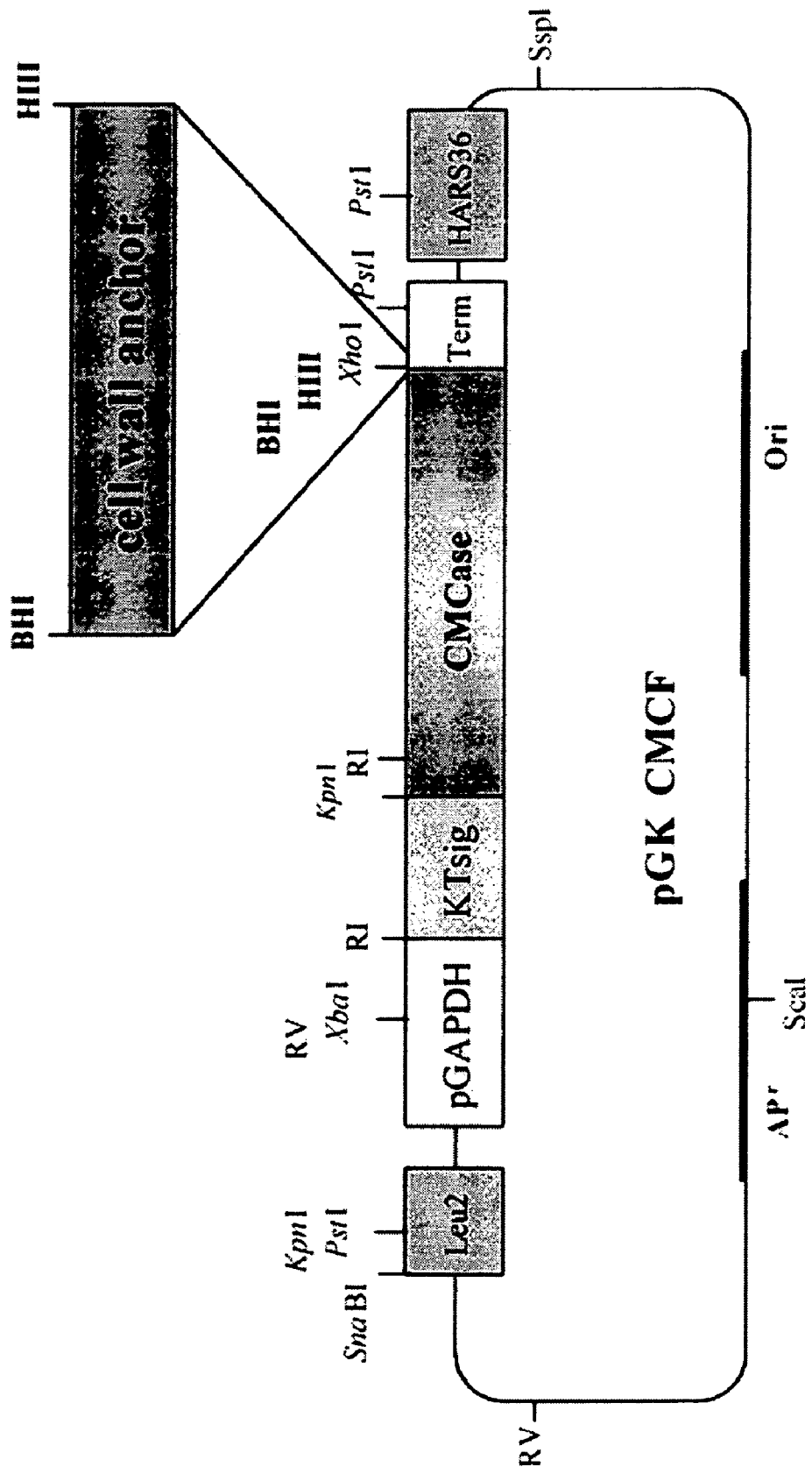
FIG. 6 is a schematic diagram showing a surface expression vector for expressing CMCase on the cell surface of *Hansenula polymorpha*, which contains a GAPDH promoter (pGAPDH), a killer toxin signal sequence (KTsig) and a CMCase gene with a termination codon (Term).

In this regard, a GAPDH promoter (Sohn et al., *Appl. Microbiol. Biotechnol.*, 1999, 51, 800) and a killer toxin signal sequence (Sor, F. and Fukuhara, *Curr. Genet.*, 1985, 9, 147) were inserted into an AMIpL1 vector (Agaphonov et al., *Yeast*, 1999, 15, 541). Then, the CMCase gene was fused in frame to give a CMCase surface expression vector, named pGK CMCF, which could express CMCase under the control of the GAPDH promoter, as shown in FIG. 6. The CMCase gene stretch corresponding to an amino acid sequence from glycine at position 31 to aspartic acid at position 355 was obtained by PCR and linked downstream of the killer toxin signal sequence in the expression vector. As seen in FIG. 6, mediator genes were inserted into the carboxyl region of the CMCase gene between the recognition sites of restriction enzymes BamHI/HindIII. Also, the expression vector was designed to have an ARS, HARS36 which directs the integration of vector to the telomeric regions of the chromosome of a host cell, so that comparison could be made of the translocation efficiency of surface anchor proteins (Sohn et al., *J. Bacteriol.*, 1996, 178, 4420).

Four putative GPI-anchor protein genes, HpCWP1, HpGAS1, HpTIP1 and HpSED1 gene fragments, were amplified from the recombinant vectors by PCR using appropriate primer sets designed to provide BamHI and HindIII sites for the PCR products. The amplified putative GPI-anchor protein genes were inserted to the expression vector pGK CMCF at the BamHI/HindIII site located in the carboxy terminal region of the CMCase gene to construct CMCase surface expression vectors for HpCWP1, HpGAS1, HpTIP1 and HpSED1, named CwpF, GasF, TipF and SedF, respectively.

Using primer sets containing BamHI/HindIII sites, four nucleic acid segments, each encoding the sequence of the 40 carboxy-terminal amino acids of each protein, were amplified by PCR, and inserted into the expression vector to construct CMCase surface expression vectors, named Cwp40, Gas40, Tip40 and Sed40, respectively.

For comparison of the surface anchoring efficiency, a DNA fragment, which encodes a carboxy-terminal sequence of 92 amino acids of Cwp2p, known as a GPI-anchor protein from *S. cerevisiae* excellent in anchoring efficiency, was synthesized by PCR and inserted into the same vector to construct a CMCase surface expression vector for Cwp2p, named ScCwp2, which was used as a control.

CMCase surface expression vectors containing the mediator protein genes were transformed into *Hansenula polymorpha* DL1-L (Hill et al., *Nucl. Acids Res.*, 1991, 19, 5791) and the transformants were selected in minimal synthetic media (2% glucose, 0.67% amino acid-free yeast nitrogen base, various amino acids with appropriate concentrations) devoid of leucine.

<2-2> Measurement of Surface Anchored CMCase Activity

Each of the selected clones was inoculated in a YPD medium (2% glucose, 2% peptone, 1% yeast extract) and cultured at 37° C. for 18 hours, after which the CMCase activity of the supernatant and the whole cell fraction were measured according to the DNS (dinitrosalicylic acid) method (G. L. Miller, *Anal, Biochem.*, 1959, 31, 426).

To test the CMCase activity, the culture broth was divided into a supernatant and a whole cell fraction by centrifugation. The whole cell fraction, after being washed twice with a citrate buffer (10 mM citrate buffer, pH 5.0), was suspended in the same buffer. The resulting suspension was added in a 1% CMC (carboxy methyl cellulose) solution and incubated at 55° C. for 30 min. Reaction was stopped by boiling for 5 min in a DNS solution, followed by the measurement of absorbance at 550 nm. The results are given in Table 1, below. The enzyme activity of CMCase was defined by U, and one U is the amount of enzyme activity which releases 1μ mole of glucose from CMC for 1 min.

TABLE 1

Surface Expression Activity of CMCase According to anchoring Mediator

| Anchoring Mediator | Activity in Supernatant (U/ml) | Activity in Whole Cell Fractio (U/ml) |
|---|---|---|
| Sed40 | 0.40 | 0.059 |
| SedF | 0.41 | 0.030 |
| Tip40 | 0.92 | 0.090 |
| TipF | 0.45 | 0.024 |
| Gas40 | 0.19 | 0.010 |
| GasF | 0.61 | 0.080 |
| Cwp40 | 1.10 | 0.150 |
| CwpF | 0.65 | 0.110 |
| MCMC | 0.14 | 0.003 |
| CMC* | 1.92 | 0.000 |
| ScCwp2 | 0.15 | 0.020 |
| DL1 | 0.00 | 0.000 |

MCMC: Transformant harboring a CMCase expression vector with no secretion signal sequence.
CMC*: Transformant harboring a CMCase expression vector with a secretion signal sequence, a CMCase gene, and a stop codon instead of anchoring mediators
DL1: wild type cell with no expression vector.

Figure 7:
FIG. 7 is a histogram showing the CMCase activity detected on the cell surface of *Hansenula polymorpha* according to surface expression mediators.

In supernatants fraction, high CMCase activity was observed. This was believed to be attributed to the fact that the CMCase expressed by the action of the GAPDH promoter was too much to properly anchored on the cell surface. Also, CMC, used as a substrate for CMCase activity assay, has the high molecular weight, so the enzyme anchored in the cell could not be effectively accessed to CMC. In whole cell fractions, the strains transformed with the vectors containing the mediator genes exhibit significantly improved CMCase activity, compared to those transformed with control vectors, MCMC devoid of the secretion signal sequence, and CMC* which had no mediator genes, thus demonstrating that CMCase was exported to the cell surface by each mediator. In addition, in transformant strains containing Tip40, GasF, Cwp40p and CwpF, CMCase were found to translocate to the cell surface at higher efficiency than those containing other mediators, as depicted in FIG. 7.

Figure 8:
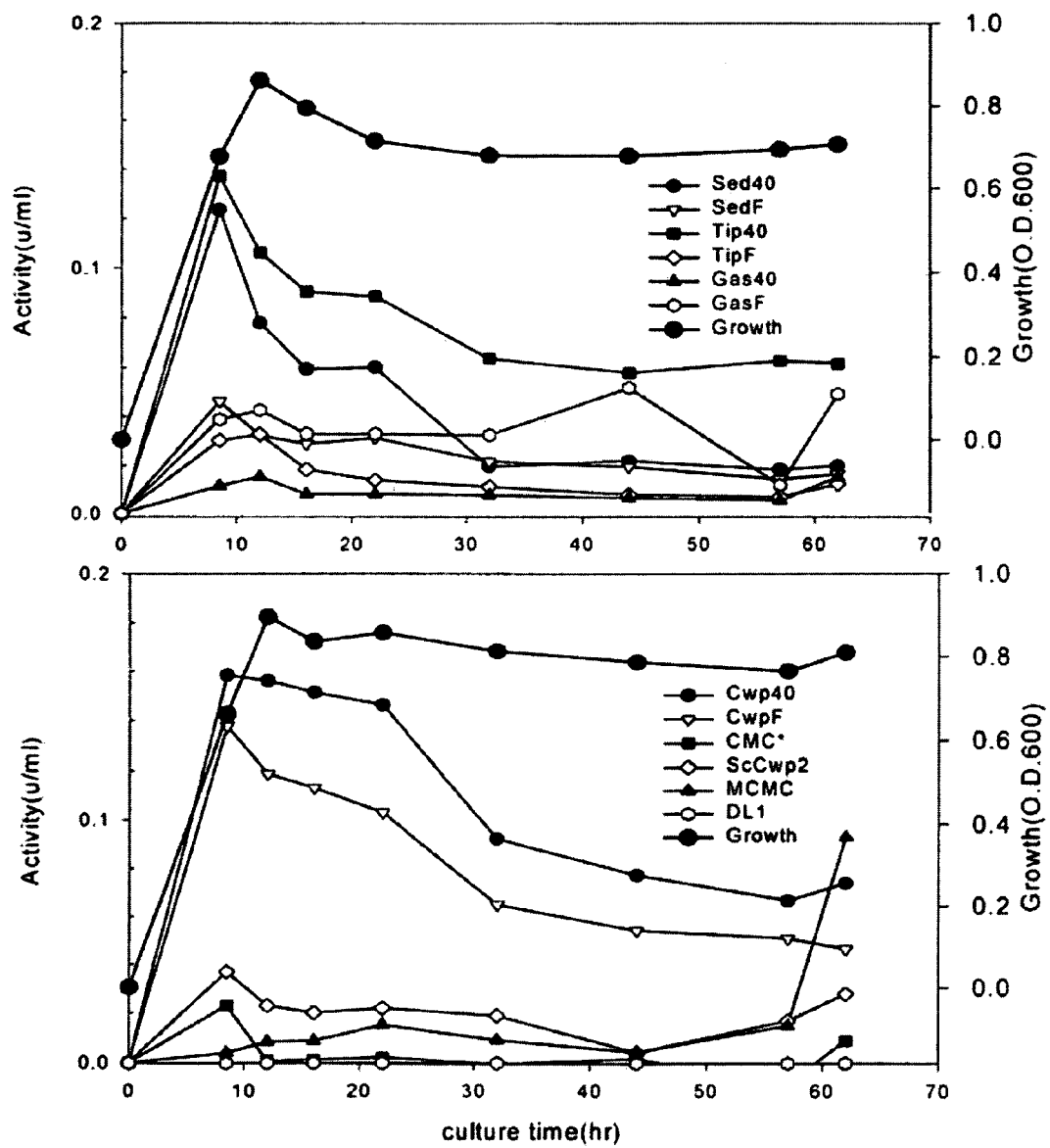
FIG. 8 shows graphs in which the CMCase activity detected on cell surfaces of *Hansenula polymorpha* strains, which have surface expression mediators is plotted with respect to culture time period.

CMCase activity was also monitored with regard to culture time periods, and the results are graphed in FIG. 8. CMCase activity tended to decrease in most of the cells when they reached the stationary phase. But the CMCase activity of the cells, which harbored the surface expression vector having the HpCWP1 gene, although being lowered in the stationary phase, was found to remain high throughout the culturing period in the whole cell fraction. Therefore, HpCwp1p is inferred to be the most stable mediator among the proteins tested, as depicted in FIG. 8.

From the data obtained, HpCwp1p was identified to be superior in surface expression efficiency and stability among the novel four GPI-anchor proteins isolated from *Hansenula polymorpha*.

Example 3

Surface Expression System Using HpPir2p

<3-1> Construction of Surface Expression System

Figure 9:
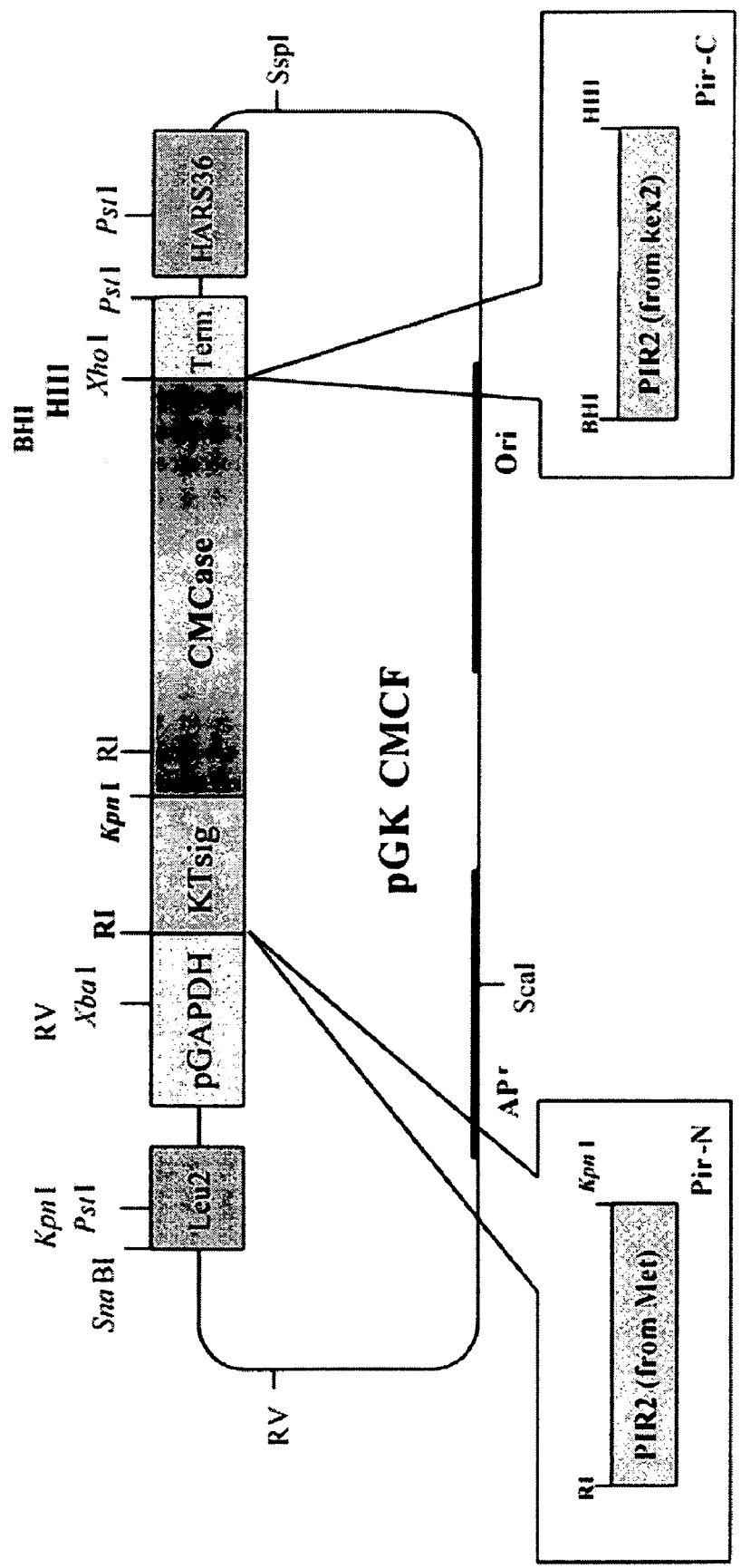
FIG. 9 is a schematic diagram showing a surface expression vector for expressing the protein HpPir2p on the cell surface of *Hansenula polymorpha*, which contains a GAPDH promoter (pGAPDH), a killer toxin signal sequence (KTsig) and a CMCase gene with a termination codon (Term), and a full length of a PIR2 gene (Pir-N) fused to the amino terminus of the killer toxin signal sequence (KTsig) or a partial fragment of a PIR2 gene (Pir-C) fused to the carboxy terminus of the CMCase gene.

A surface expression vector was constructed in which the HpPIR2 gene encoding a cell wall expression protein different from GPI-anchor proteins was used as a mediator for surface expression of foreign proteins with CMCase as a reporter. To determine which part of the protein HpPir2p is useful for expressing target proteins on the cell wall, CMCase was fused to HpPir2p at its either termini, as shown in FIG. 9.

In order to utilize the carboxy terminus of HpPir2p for fusion with a target protein, a gene fragment encoding a polypeptide stretch ranging from the Kex2 cleavage site to the stop codon of the protein HpPir2p was synthesized by PCR and inserted to the expression vector, pGK CMCF constructed in Example 2, at the restriction enzyme sites (BamHI/HindIII) to give a recombinant expression vector, named Pir-C. In the case of the amino terminus of HpPir2p, the expression vector, pGK CMCF was deprived of the killer toxin signal sequence and replaced with a gene fragment encoding the full length of the open reading frame from the initiator methionine to the stop codon of the HpPir2p, so as to fuse HpPIR2 gene directly to the amino terminus of CMCase. The resulting surface expression vector was named Pir-N. The expression vectors were transformed into *Hansenula polymorpha*, followed by selecting transformants in the same manner as in above.

<3-2> Activity Measurement of Surface Anchored CMCase

The CMCase activity of the transformants selected in Example 3-1 was measured, after being cultured in YPD media, and the results are given in Table 2, below.

TABLE 2

CMCase Activity of *Hansenula polymorpha* Using HpPir2p as Surface Expression Mediator

| Mediator | Activity in Supernatant (U/ml) | Activity in Whole Cell Fraction (U/ml) |
|---|---|---|
| Pir-C #1 | 3.33 | 0.010 |
| Pir-C #2 | 2.80 | 0.009 |
| Pir-N #1 | 1.83 | 0.080 |
| Pir-N #2 | 1.86 | 0.084 |
| CMC* | 2.53 | 0.000 |

As shown in Table 2, almost the same CMCase activity was measured when the carboxy-terminal region of the protein HpPir2p was used as mediator (Pir-C), as when a CMCase gene with a stop codon was used, indicating that the carboxy-terminal region of the protein HpPir2p was completely deficient in surface anchoring ability. Also, the CMCase activity was not affected by the insertion of the protein HpPir2P. By contrast, where the amino-terminal region of the protein HpPir2p was used as a mediator (Pir-N), CMCase activity was detected not only in the supernatant, but also in the whole cell fraction, demonstrating that the CMCase was expressed on the cell wall.

Therefore, the protein HpPir2p was anchored in the cell wall and thus could be used as a surface expression mediator. Over conventional GPI-anchor proteins, the protein HpPir2p has the advantage of linking the amino terminus of a target protein to its carboxy terminus. This anchoring protein is useful to avoid the problem of the activity loss took place when the target protein has an active site in its carboxy-terminal region.

Example 4

Surface Expression System Using HpWsc1p

<4-1> Construction of Surface Expression System

The protein HpWsc1p is composed of a transmembrane domain by which the protein is anchored in the cell membrane, a serine/threonine-rich domain that traverses the cell wall, and an amino-terminal cystein motif which exists in the extracellular space, functioning to detect external signals (Verna et al., *Proc. Natl. Sci. USA*, 1997, 13804), as illustrated in FIG. 10a.

In this example, the HpWSC1 gene was used for constructing a surface expression system. In this regard, CMCase was fused to the amino terminus of HpWsc1p and used as a reporter protein exposed on the cell surface.

To identify which domain is responsible for cell wall anchoring, truncated HpWSC1 gene fragments were synthesized by PCR using primer sets designed to have BamHI/HindIII sites. Four truncated HpWSC1 gene fragments, devoid of either the cystein motif (wsc-t) or the transmembrane domain (Wsc-c), and of both of them (Wsc-o), and an intact WSC1 gene (Wsc-ct) encoding the full length of HpWSC1, were inserted at the BamHI/HindIII site of the plasmid vector (see FIG. 10b). The recombinant vectors were transformed into *Hansenula polymorpha* DL1-L, followed by selecting transformants in the same manner as in above.

<4-2> Activity Measurement of Surface Anchored CMCase

After 18 hours culture in YPD broth, the CMCase activity of the selected transformants was measured according to the DNS method, and the results are given in Table 3, below.

TABLE 3

CMCase Activity of *Hansenula polymorpha* Strains Using HpWsc1p as Expression Mediator

| Expression Mediator | Activity in Supernatant (U/ml) | Activity in Whole Cell Fraction (U/ml) |
|---|---|---|
| Wsc-c | 0.90 | 0.002 |
| Wsc-ct | 0.35 | 0.069 |
| Wsc-o | 2.40 | 0.003 |
| Wsc-t | 0.04 | 0.006 |
| CMC* | 2.54 | 0.000 |
| DL1 | 0.00 | 0.000 |

As seen in Table 3, only when the transmembrane domain was presented in the fusion protein (Wsc-ct, Wsc-t), the CMCase was not secreted, but rather remained attached to the cell. However, although the transmembrane domain was present, CMCase activity was not detected in the whole cell fraction if the cystein motif was absent (Wsc-o, Wsc-t). The result was believed to be attributed to the fact that the CMCase was not sufficiently exposed on the cell surface. In contrast, when the transmembrane domain was absent (Wsc-o, Wsc-c), the CMCase activity was mostly detected in the supernatant. In addition, the cystein motif was found to make an additional contribution to the secretion of the CMCase.

Therefore, the mediator derived from the HpWsc1p must have both, the cystein motif and the transmembrane domain for anchoring efficiency. As the activity detected in the whole cell fraction was almost the same as in the case of GPI-anchor proteins, the HpWsc1p was suggested as a novel mediator for expression proteins on the cell surface.

Example 5

Surface Expression of Glucose Oxidase

<5-1> Construction of Surface Expression System

Among the mediator proteins tested, three GPI-anchor proteins, HpTip1p (Tip40), HpGas1p (GasF) and HpCwp1p (CwpF), and the HpWsc1p (Wsc-ct) were tested for the surface expression of glucose oxidase. For the surface expression of glucose oxidase, a glucoamylase signal sequence and a glucose oxidase gene were synthesized by PCR and fused to each other before being cloned into pBluescript II SK(+). pGK CMCF vectors in which the expression mediator genes were included were treated with EcoRI and BamHI to remove the killer toxin signal sequence and the CMCase gene, followed by the insertion of the glucose oxidase expression cassette to give a surface expression vector pGA GOD. This vector was transformed into *Hansenula polymorpha* DL1-L and transformants were selected in the same manner as in the above CMCase case.

<5-2> Activity Assay of Surface Anchored Glucose Oxidase

The transformants selected in Example 5-1 were transferred onto YPD plate media and measured for glucose oxidase activity according to the plate activity assay method using peroxidase and O-dianisidine (Hodgkins et al., *Yeast*, 1993, 9, 625). As shown in FIG. 11, a smaller glucose oxidase activity circle was formed when expressing glucose oxidase with the anchoring mediators (Tip40, GasF, CwpF and Wsc-ct) than glucose oxidase without them (GOD*).

After being cultured in YPD media, the transformants, which were identified to have glucose oxidase activity on the cell surface by the plate activity assay method, were subjected to FACS analysis along with the wild type. The FACS results are given in FIG. 12. In this regard, the cultured cells were washed twice with phosphate buffered saline (PBS, pH 6.5) and suspended in PBS containing 1% BSA (bovine serum albumin). The suspension was added with a glucose oxidase antibody (Accurate Chemicals) and allowed to stand for 1 hour on ice, after which the cells were washed three times with the same buffer and resuspended. A secondary antibody (FITC-labeled anti-rabbit antibody, Sigma) was added to the suspension which was incubated on ice for 30 min, followed by washing the cells three times with the same buffer.

Figure 12:
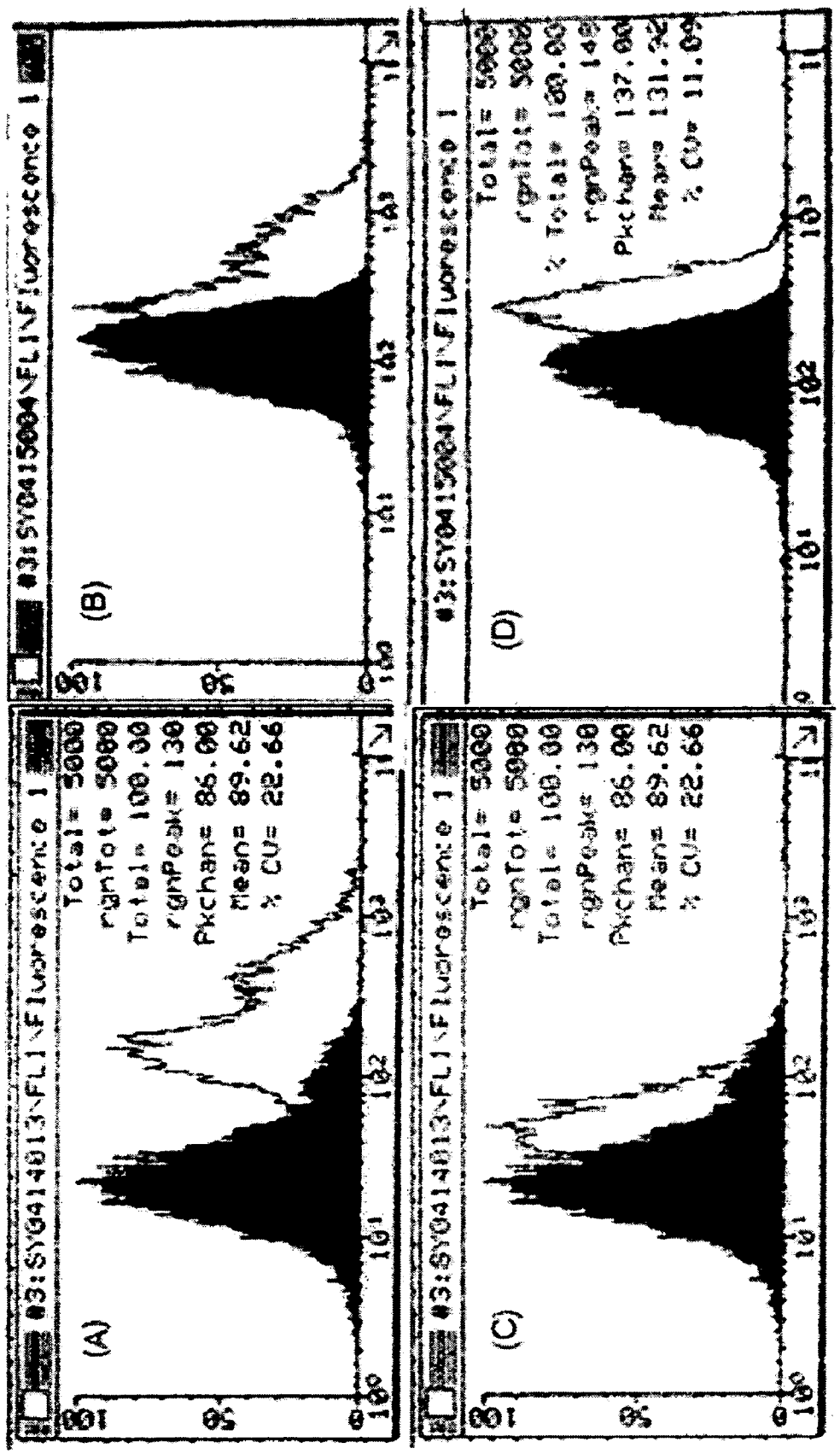
FIG. 12 shows FACS analysis results of *Hansenula polymorpha* strains (white) on which glucose oxidase is expressed by employing surface expression mediators such as CwpF (panel A). Tip40 (panel B), GasF (panel C), and Wsc-ct (panel D), along with a wild type (gray).

In all cases of using the anchoring mediators, fluorescent cells were observed by FACS (fluorescence activated cell sorter) analysis, indicating that the glucose oxidase was expressed and anchored onto the cell surface. Additionally, higher glucose oxidase activity was detected in the whole cell fraction than in the supernatant throughout all of the strains. On the whole, the activity of surface anchored glucose oxidase was found to agree with that of CMCase. When CwpF was employed, fluorescence was detected from a large number of cells, demonstrating that CwpF had an excellent cell wall anchoring activity. It was also found that Tip40 was efficient in expression proteins in cell surfaces, as analyzed by FACS (FIG. 12). Under the mediation of GasF and Wsc-tc, fluorescence, as evidence of the cell wall anchoring, was detected, but in a low level, which resulted, to our knowledge, from the fact that GasF and Wsc-tc both are cytoplasmic membrane proteins so that their exposure on the cell surface is poor compared to the other mediators. However, even in this case, there seems to be no problem in detecting the activity of the enzyme if the substrate penetrates the cell wall.

The assay results obtained from two enzymes anchored in the cell wall by use of various mediators, taken together, demonstrates that HpCwp1p is the most effective surface anchoring mediator among the GPI-anchor proteins and the proteins HpPir2p and HpWsc1p can be suggested as novel surface anchoring mediators.

Example 6

Surface Expression System Using Glucoamylase Gene

<6-1> Construction of Surface Expression System

A known cell wall protein was investigated as to its usefulness as an expression mediator. The glucoamylase gene STA1, derived from *Saccharomyces diastaticus*, was obtained and studied for its usefulness to construct a surface expression system in *Saccharomyces cerevisiae*.

To begin with, various truncated STA1 gene fragments were synthesized by PCR using appropriate primers and inserted to pBluescript II SK(+) at EcoRI and SmaI sites. The cloning was confirmed by DNA sequencing. The recombinant vectors were digested with EcoRI and HindIII to create the site to which the GAPDH promoter of *Saccharomyces cerevisiae* could be inserted. After completion of the insertion, the digestion of the recombinant vectors with KpnI and EheI made various STA1 genes fused with the GAPDH promoter, which were inserted into the expression vector YEp352 (Hill et al., *Yeast*, 1986, 2, 163) at KpnI/PstI sites to construct CMCase surface expression vectors.

With reference to FIG. 13, there are shown vector diagrams for the surface expression systems using the STA1 gene. As depicted, the surface expression systems were constructed with vectors comprising the signal sequence only (STASS), both of the signal sequence and the octapeptide sequence (STASS-8), all of the signal sequence, the octapeptide sequence and the threonine/serine-rich domain (STASS-8-TS), both of the signal sequence and the threonine/serine-rich domain (STASS-TS), both of the signal sequence and alpha-agglutinin (STASS-CMC-Agalc), and all of the signal sequence, the octapeptide, and alpha-agglutinin (STASS-8-CMC-Agalc), along with a CMCase gene as a reporter gene. The CMCase gene was synthesized by PCR, cut with SmaI/PstI and inserted into the expression vectors. The resulting expression vectors were introduced into *Saccharomyces cerevisiae* L3262, which were then cultured in a minimal plate medium deficient in uracil to select the transformant, which harbored the expression vectors.

<6-2> Activity Measurement of Surface Anchored CMCase

The transformants selected in Example 6-1 were assayed for CMCase activity after being cultured at 30° C. for 48 hours in YPD media. The assay for CMCase activity was conducted by the pNPC (p-nitrophenyl β-D-cellobiocide) method (Deschpande et al., *Anal. Biochem.*, 1984, 138, 481). For this, the culture broth of each transformant was fractioned into a supernatant and a whole cell fraction by centrifugation. The cell mass was washed three times with PBS and suspended in PBS. The suspension was mixed with a 2.5 mM pNPC solution and incubated at 37° C. for 1 hour, followed by adding an equal volume of 2% sodium carbonate ($Na_2CO_3$) to stop the reaction. Absorbance was measured at 410 nm, and the results are given in Table 4, below. In Table 4, the enzyme activity of CMCase was defined by U, one U being defined as the amount enzyme activity to releases 1µ mole of pNP for 1 min.

TABLE 4

CMCase Activity in *Saccharomyces cerevisiae*

|  | ss-CMC | ss8-CMC | ssts-CMC | ss8ts-CMC |
|---|---|---|---|---|
| Activity in Supernatant (U/l) | 339 | 389 | 189 | 145 |
| Activity in Whole Cell Fraction (U/l) | 13.6 | 14.5 | 112 | 128 |
| Activity in Whole Cell Fraction Activity in Supernatant (%) | 3.9 | 3.6 | 37 | 47 |

As shown in Table 4, when employing the signal sequence only (SS-CMC), most of the CMCase was secreted extracellularly, not anchored in the cell wall. In contrast, when employing the threonine/serine-rich domain linked directly to the signal sequence (SS-TS-CMC) or when employing the threonine/serine-rich domain linked to the signal sequence via the octapeptide sequence (SS-8-TS-CMC), the enzyme activity was measured to be low in the supernatant, but high in the whole cell fraction.

Figure 14:
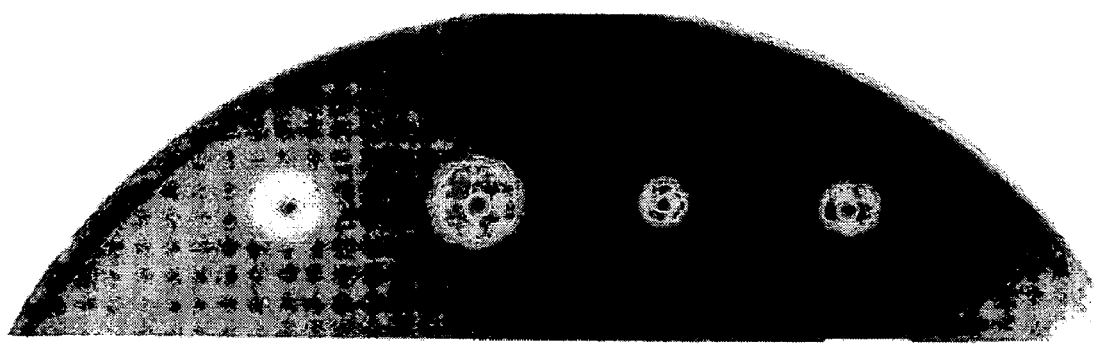
FIG. 14 is a photograph showing the CMCase activity measured according to the plate activity assay method from *Saccharomyces cerevisiae* strains which harbor the signal sequence only (SS), both of the signal sequence and the octapeptide sequence (SS-8), all of the signal sequence, the octapeptide sequence and the threonine/serine-rich domain (SS-8-TS), and both of the signal sequence and the threonine/serine-rich domain (SS-TS).

The same results were confirmed by plate activity assay, as shown in FIG. 14. Large circles were formed around the colonies, which harbored the signal sequence only (SS), as most of the expressed enzyme was extracellularly secreted.

In contrast, the presence of the threonine/serine-rich domain hindered the enzyme secretion as proven by the small circles formed around the colonies.

To confirm the transport of CMCase to the cell surface, FACS analysis for CMCase was conducted in the same manner as in *Hansenula polymorpha*. The results are given in FIG. 15. As observed by the FACS diagrams, fluorescence was detected in the cells harboring the threonine/serine-rich domain, suggesting the presence of CMCase on the cell surface. Meanwhile, after CMCase was fused to the carboxy terminus of α-agglutinin, CMCase activity was measured to test the surface anchoring ability. However, CMCase activity in this case was not higher than in case using only the threonine/serine-rich domain. Therefore, the threonine/serine-rich domain of the STA1 gene alone was identified to function as a good surface anchoring mediator.

Thus, when used for the construction of surface expression systems, glucoamylase or its domains could be fused to the amino terminus of a target protein. Thus, these systems may circumvent the problems arising when a carboxy-terminal active domain of the target protein is interrupted by the mediator fused to the carboxy terminus. Therefore, the mediators described herein allow the development of surface expression systems capable of expressing various types of target proteins, according to the characteristics of the target proteins.

INDUSTRIAL APPLICABILITY

As described hereinbefore, surface expression proteins derived from *Hansenula polymorpha*, an industrially useful methylotropic yeast, are highly effective in construction of surface expression systems and development of biocatalyst application systems. Because of their ability to produce industrially useful biomaterials, such as enzymes, antigens, antibodies, etc., and to offer industrial production tools such as immobilized biocatalysts, the surface expression systems established in the present invention can find numerous applications in various industries, including the medical industry, the food industry and the chemical and biochemical industry.

The present invention has been described in an illustrative manner, and it is to be understood that the terminology used is intended to be in the nature of description rather than of limitation. Many modifications and variations of the present invention are possible in light of the above techniques. Therefore, it is to be understood that within the scope of the appended claims, the invention may be practiced otherwise than as specifically described.

What is claimed is:

1. An isolated polynucleotide comprising the sequence of SEQ. ID. NO: 7.

2. An *E. coli* transformant transformed with a recombinant vector containing 6 kb Sal I fragment comprising the polynucleotide of claim 1 and deposited with Accession No. KCTC 0826BP.

3. A surface expression system for expressing a heterologous polypeptide or protein on the surface of a yeast cell, wherein the polypeptide encoded by the polynucleotide of claim 1, or a fragment of the polypeptide consisting of amino acids at positions 42–81 of SEQ ID NO: 15, is used as an expression mediator wherein said polypeptide or fragment localizes the heterologous polypeptide or protein onto said surface.

4. The surface expression system according to claim 3, wherein the yeast cell is selected from the group consisting of yeast spp., including *Candida* spp., *Debaryomyces* spp., *Hansenula* spp., *Kluyveromyces* spp., *Pichia* spp., *Schizosaccharomyces* spp., *Yarrowia* spp., *Saccharomyces* spp.

5. The surface expression system according to claim 3, wherein the heterologous polypeptide is fused to the N-terminus of the expression mediator.

6. The isolated polynucleotide according to claim 1, wherein the polynucleotide encodes *Hansenula polymorpha* Cell Wall Protein 1 having the sequence of SEQ ID NO: IS.

7. The isolated polynucleotide according to claim 1, wherein the polynucleotide is isolated from *Hansenula polymorpha*.

8. The isolated polynucleotide of claim 1 that is DNA.

* * * * *